United States Patent
Field

(10) Patent No.: US 9,125,721 B2
(45) Date of Patent: Sep. 8, 2015

(54) ACTIVE DRAINAGE SYSTEMS WITH DUAL-INPUT PRESSURE-DRIVEN VALVES

(71) Applicant: Alcon Research, Ltd., Fort Worth, TX (US)

(72) Inventor: Leslie A Field, Portola Valley, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 276 days.

(21) Appl. No.: 13/710,565

(22) Filed: Dec. 11, 2012

(65) Prior Publication Data
US 2013/0150779 A1    Jun. 13, 2013

Related U.S. Application Data

(60) Provisional application No. 61/569,976, filed on Dec. 13, 2011.

(51) Int. Cl.
*A61F 9/00* (2006.01)
*A61F 9/007* (2006.01)
(Continued)

(52) U.S. Cl.
CPC ............. *A61F 9/00781* (2013.01); *F16K 7/17* (2013.01); *F16K 31/126* (2013.01)

(58) Field of Classification Search
CPC ...... F16K 7/17; F16K 31/126; A61F 9/00781
USPC ............ 137/81.1, 494, 505, 505.14; 251/61, 251/61.1, 61.2; 604/9
See application file for complete search history.

(56) References Cited

U.S. PATENT DOCUMENTS

| | | | |
|---|---|---|---|
| 4,089,329 A | | 5/1978 | Couvillon et al. |
| 4,206,762 A | | 6/1980 | Cosman |
| 4,300,748 A | * | 11/1981 | Kreeley ............................ 251/5 |

(Continued)

FOREIGN PATENT DOCUMENTS

| | | |
|---|---|---|
| EP | 0102747 A1 | 3/1984 |
| EP | 1195523 A2 | 4/2002 |

(Continued)

OTHER PUBLICATIONS

"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine."

(Continued)

*Primary Examiner* — Matthew W Jellett
(74) *Attorney, Agent, or Firm* — Haynes and Boone, LLP

(57) ABSTRACT

A pressure-driven valve is disclosed. The valve includes a housing and a flow control portion disposed within the housing. The housing includes a fluid inlet and a fluid outlet. The flow control portion has a first side subject to fluid flow pressure in a fluid flow channel, and a second side subject to an outlet pressure representative of pressure at the fluid outlet. The flow control portion is deformable to increase and decrease flow through the fluid flow channel based on pressure differentials between the fluid flow pressure, a tube pressure, and the outlet pressure. In some instances, the flow control portion comprises a flow control membrane and a radially-fluctuating pressure tube attached to the periphery of the membrane.

18 Claims, 6 Drawing Sheets

(51) Int. Cl.
*F16K 31/126* (2006.01)
*F16K 7/17* (2006.01)

(56) References Cited

U.S. PATENT DOCUMENTS

| | | | |
|---|---|---|---|
| 4,310,140 A * | 1/1982 | Boomer et al. | 251/5 |
| 4,457,757 A | 7/1984 | Molteno | |
| 4,604,087 A | 8/1986 | Joseph | |
| 4,656,827 A | 4/1987 | Puillet | |
| 4,750,901 A | 6/1988 | Molteno | |
| 4,794,940 A * | 1/1989 | Albert et al. | 137/1 |
| 4,858,883 A * | 8/1989 | Webster | 251/61.1 |
| 4,869,282 A | 9/1989 | Sittler et al. | |
| 4,922,913 A | 5/1990 | Waters et al. | |
| 5,005,577 A | 4/1991 | Frenkel | |
| 5,083,742 A | 1/1992 | Wylie et al. | |
| 5,178,604 A | 1/1993 | Baerveldt | |
| 5,179,953 A | 1/1993 | Kursar | |
| 5,397,300 A | 3/1995 | Baerveldt | |
| 5,466,233 A | 11/1995 | Weiner et al. | |
| 5,476,445 A | 12/1995 | Baerveldt | |
| 5,558,629 A | 9/1996 | Baerveldt | |
| 5,573,646 A | 11/1996 | Saito et al. | |
| 5,626,558 A | 5/1997 | Suson | |
| 5,681,275 A | 10/1997 | Ahmed | |
| 5,702,618 A | 12/1997 | Saaski et al. | |
| 5,707,643 A | 1/1998 | Ogura et al. | |
| 5,891,097 A | 4/1999 | Saito et al. | |
| 5,910,110 A | 6/1999 | Bastable | |
| 6,007,511 A | 12/1999 | Prywes | |
| 6,048,328 A | 4/2000 | Haller et al. | |
| 6,251,090 B1 | 6/2001 | Avery et al. | |
| 6,443,893 B1 | 9/2002 | Schnakenberg et al. | |
| 6,447,449 B1 | 9/2002 | Fleischman et al. | |
| 6,468,283 B1 | 10/2002 | Richter et al. | |
| 6,533,733 B1 | 3/2003 | Ericson et al. | |
| 6,579,235 B1 | 6/2003 | Abita et al. | |
| 6,589,198 B1 | 7/2003 | Soltanpour et al. | |
| 6,682,500 B2 | 1/2004 | Soltanpour et al. | |
| 6,712,764 B2 | 3/2004 | Jeffries et al. | |
| 6,719,750 B2 | 4/2004 | Varner et al. | |
| 6,749,568 B2 | 6/2004 | Fleischman et al. | |
| 6,830,229 B2 * | 12/2004 | Wetzel et al. | 251/30.02 |
| 6,939,299 B1 | 9/2005 | Petersen et al. | |
| 6,976,982 B2 | 12/2005 | Santini et al. | |
| 7,137,952 B2 | 11/2006 | Leonardi et al. | |
| 7,169,106 B2 | 1/2007 | Fleischman et al. | |
| 7,252,006 B2 | 8/2007 | Tai et al. | |
| 7,304,334 B2 | 12/2007 | Agarwal et al. | |
| 7,354,416 B2 | 4/2008 | Quiroz-Mercado et al. | |
| 7,409,863 B2 | 8/2008 | Bateman et al. | |
| 7,607,641 B1 * | 10/2009 | Yuan | 251/331 |
| 7,612,328 B2 | 11/2009 | Kaiser | |
| 7,648,465 B2 | 1/2010 | Gordon | |
| 7,756,559 B2 | 7/2010 | Abreu | |
| 7,824,699 B2 | 11/2010 | Ralph et al. | |
| 8,182,435 B2 | 5/2012 | Dacquay et al. | |
| 8,206,440 B2 | 6/2012 | Guarnieri | |
| 8,257,295 B2 | 9/2012 | Rickard et al. | |
| 8,419,673 B2 | 4/2013 | Rickard | |
| 8,549,925 B2 | 10/2013 | Tai et al. | |
| 8,814,820 B2 | 8/2014 | Bergheim et al. | |
| 2001/0000527 A1 | 4/2001 | Yaron et al. | |
| 2002/0019607 A1 | 2/2002 | Bui | |
| 2002/0087111 A1 | 7/2002 | Ethier et al. | |
| 2002/0099359 A1 | 7/2002 | Santini, Jr. et al. | |
| 2002/0103412 A1 | 8/2002 | Trimmer | |
| 2002/0139947 A1 | 10/2002 | Wang | |
| 2002/0143284 A1 | 10/2002 | Tu et al. | |
| 2002/0175191 A1 | 11/2002 | Joshi et al. | |
| 2002/0193674 A1 | 12/2002 | Fleischman et al. | |
| 2003/0014036 A1 | 1/2003 | Varner et al. | |
| 2003/0078487 A1 | 4/2003 | Jeffries et al. | |
| 2003/0225318 A1 | 12/2003 | Montegrande et al. | |
| 2004/0013702 A1 | 1/2004 | Glover | |
| 2004/0059248 A1 | 3/2004 | Messner et al. | |
| 2004/0073137 A1 | 4/2004 | Lloyd et al. | |
| 2004/0111050 A1 | 6/2004 | Smedley et al. | |
| 2004/0186367 A1 | 9/2004 | Fresco | |
| 2004/0254438 A1 | 12/2004 | Chuck et al. | |
| 2004/0254517 A1 | 12/2004 | Quiroz-Mercado et al. | |
| 2005/0049578 A1 | 3/2005 | Tu et al. | |
| 2005/0159660 A1 | 7/2005 | Montegrande et al. | |
| 2005/0271704 A1 | 12/2005 | Tu et al. | |
| 2005/0273033 A1 | 12/2005 | Grahn et al. | |
| 2006/0041220 A1 | 2/2006 | Boukhny et al. | |
| 2006/0131350 A1 | 6/2006 | Schechter et al. | |
| 2007/0019156 A1 | 1/2007 | Fink | |
| 2007/0032757 A1 | 2/2007 | Medow | |
| 2007/0077270 A1 | 4/2007 | Wen | |
| 2007/0106199 A1 | 5/2007 | Krivoy et al. | |
| 2007/0106200 A1 | 5/2007 | Levy | |
| 2007/0109117 A1 | 5/2007 | Heitzmann et al. | |
| 2007/0123767 A1 | 5/2007 | Montegrande et al. | |
| 2007/0129623 A1 | 6/2007 | Fleischman et al. | |
| 2007/0156079 A1 | 7/2007 | Brown | |
| 2007/0212397 A1 | 9/2007 | Roth | |
| 2007/0255262 A1 | 11/2007 | Haase | |
| 2008/0015421 A1 | 1/2008 | Penner | |
| 2008/0027478 A1 | 1/2008 | Connors et al. | |
| 2008/0077127 A1 | 3/2008 | Gao et al. | |
| 2008/0097276 A1 | 4/2008 | Bertrand et al. | |
| 2008/0129486 A1 | 6/2008 | Jeckelmann et al. | |
| 2008/0147021 A1 | 6/2008 | Jani | |
| 2008/0228127 A1 | 9/2008 | Burns et al. | |
| 2008/0257915 A1 | 10/2008 | Wold | |
| 2009/0076367 A1 | 3/2009 | Sit et al. | |
| 2009/0227933 A1 | 9/2009 | Karageozian | |
| 2009/0240215 A1 | 9/2009 | Humayun et al. | |
| 2009/0275924 A1 | 11/2009 | Lattanzio et al. | |
| 2010/0010416 A1 | 1/2010 | Juan, Jr. et al. | |
| 2010/0042209 A1 | 2/2010 | Guarnieri | |
| 2010/0174272 A1 | 7/2010 | Weiner | |
| 2010/0222769 A1 | 9/2010 | Meng et al. | |
| 2010/0222770 A1 | 9/2010 | Gordon et al. | |
| 2010/0234717 A1 | 9/2010 | Wismer | |
| 2010/0305550 A1 | 12/2010 | Meng et al. | |
| 2011/0046536 A1 | 2/2011 | Stegmann et al. | |
| 2011/0071454 A1 | 3/2011 | Dos Santos et al. | |
| 2011/0071456 A1 | 3/2011 | Rickard | |
| 2011/0071505 A1 | 3/2011 | Rickard et al. | |
| 2011/0248671 A1 | 10/2011 | Dos Santos et al. | |
| 2013/0204177 A1 * | 8/2013 | Field et al. | 604/9 |

FOREIGN PATENT DOCUMENTS

| | | |
|---|---|---|
| EP | 1917987 B1 | 5/2008 |
| JP | S6182748 A | 4/1986 |
| JP | H03049775 A | 3/1991 |
| JP | H0334943 B2 | 5/1991 |
| JP | 2002507919 A | 3/2002 |
| JP | 2004500220 A | 1/2004 |
| JP | 2005535392 A | 11/2005 |
| JP | 2007512866 A | 5/2007 |
| JP | 2008546501 A | 12/2008 |
| JP | 2009508584 A | 3/2009 |
| JP | 2009509334 A | 3/2009 |
| JP | 2009532113 A | 9/2009 |
| JP | 2010503220 A | 1/2010 |
| WO | 9303665 | 3/1993 |
| WO | 9803665 | 1/1998 |
| WO | 9803809 | 1/1998 |
| WO | 9938470 | 8/1999 |
| WO | WO 01/74427 A1 | 10/2001 |
| WO | 0194784 | 12/2001 |
| WO | 02056758 | 7/2002 |
| WO | 03102632 | 12/2003 |
| WO | WO 2004/014218 A2 | 2/2004 |
| WO | 2005088417 | 9/2005 |
| WO | WO 2005/079204 A2 | 9/2005 |
| WO | 2007127305 | 11/2007 |
| WO | 2007136993 | 11/2007 |
| WO | 2008061043 | 5/2008 |
| WO | WO 2008/060649 A2 | 5/2008 |

(56) References Cited

FOREIGN PATENT DOCUMENTS

| WO | WO 2008066485 A1 * | 6/2008 | ............... F16K 99/00 |
|---|---|---|---|
| WO | 2008084350 | 7/2008 | |
| WO | WO 2008/084350 A2 | 7/2008 | |
| WO | WO 2008/084350 A3 | 7/2008 | |
| WO | WO 2008/094672 A2 | 8/2008 | |
| WO | WO 2008/094672 A3 | 8/2008 | |
| WO | 2009010799 | 1/2009 | |
| WO | 2009026499 | 2/2009 | |
| WO | 2009049686 | 4/2009 | |
| WO | 2009081031 | 7/2009 | |
| WO | 2010129446 | 11/2010 | |
| WO | 2011034727 | 3/2011 | |
| WO | 2011034738 | 3/2011 | |
| WO | 2011034740 | 3/2011 | |
| WO | 2011034742 | 3/2011 | |
| WO | 2011035218 | 3/2011 | |
| WO | 2012012017 | 1/2012 | |
| WO | WO 2013/085894 A2 | 6/2013 | |
| WO | WO 2013/085895 A1 | 6/2013 | |
| WO | WO 2013/090231 A1 | 6/2013 | |
| WO | WO 2013/123142 A1 | 8/2013 | |

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.

Schnakenberg, U., et al, "Initial Investigations on Systems for Measuring Intraocular Pressure," Sensors and Actuators, 2000, p. 287-291, vol. 85, Elsevier Science B.V., Germany.

Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/049424, Nov. 26, 2010, 15 pages.

International Searching Authority, Search Report of the International Searching Authority, PCT/US2011/036742, Aug. 17, 2011, 2 pages.

Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.

Neagu Cristina R.; "A Medical Microactuator Based on an Electrochemical Principle"; Thesis at the Twente University,the Netherlands, Enschede; Aug. 28, 1998; pp. 1-162.

Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; Trans Am Ophthalmol Soc 2009; 107; pp. 60-71.

Erik Stemme and Goran Stemme; "A Valveless Diffuser/Nozzle-Based Fluid Pump"; ScienceDirect; Sensors and Actuators A, 39 (1993); pp. 159-167.

Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.

International Search Report and Written Opinion corresponding to PCT/US2010/047605 dated Dec. 16, 2010.

International Search Report and Written Opinion corresponding to PCT/US2010/047612 dated Dec. 21, 2010.

Driot et al.; "Ocular pharmacokinetics of fluocinolone acetonide after RetisertTM intravitreal implantation in rabbits over a 1-year period"; J. Ocular Pharm; vol. 20; No. 3; pp. 269-275 (2004).

Glybina et al.; "Neuroprotective properties of fluocinolone acetonide chronically delivered into the vitreous of albino RCS rats"; IVOD; vol. 47; ARVO E-Abstract 1028 (2006).

Kupperman et al.; "Efficacy and safety of a novel intravitreous dexamethasone drug-delivery system after applicator or incisional placement in patients with macular edema"; IVOS; vol. 47; ARVO E-Abstract 5913 (2006).

Miyamoto et al.; "Biodegradable scleral implant for intravitreal controlled release of fluconazole"; Current Eye Res.; vol. 16; No. 19; pp. 930-935 (1997).

Miruthyunjaya et al.; "An intravitreal sustained release fluocinolone acetonide device to treat severe experimental uveitis"; IVOS; vol. 44; ARVO E-Abstract 4215 (2003).

Ratanapakorin et al.; "Helical intravitreal triamcinolone implant: An explanation survival study"; IVOS; vol. 46; ARDO E-Abstract 484 (2005).

Rego et al; "In vitro evaluation of sustained-release intravitreal dexamethasone implants"; IVOS; vol. 45; ARVO E-Abstract 5060 (2004).

Sakurai et al.; "Scleral plug of biodegradable polymers containing ganciclovir for experimental cytomegalovirus retinitis"; IVOS; vol. 42; No. 9; pp. 2043-2048 (2004).

See et al.; "Safety and drug release profile of injectable intravitreal sustained-release fluocinolone acetonide device"; IVOS; vol. 47; ARVO E-Abstract 5119 (2006).

Tano et al.; "Helical intravitreal implant: surgical method development and outcomes"; IVOS; vol. 46; ARVO E-Abstract 483 (2005).

Varner et al.; "Development of a minimally invasive intravitreal implant for drug delivery"; IVOS; vol. 44; ARVO E-Abstract 4214 (2003).

(56) References Cited

OTHER PUBLICATIONS

Weiner; "Drug delivery systems in ophthalmic applications; in Ocular Therapeutics; Eye on New Discoveries; T. Yorio, A. Clark, M. Wax, Eds, Elsevier Press/Academic Press, New York", pp. 7-43 (2007).

Yasukawa et al.; "Biodegradable scleral plugs for vitreoretinal drug delivery"; Adv. Drug Del. Rev.; vol. 52; No. 1; pp. 25-36 (2001).

International Search Report and Written Opinion corresponding to PCT/US2012/068878 dated Apr. 3, 2013.

International Search Report and Written Opinion corresponding to PCT/US2012/067747 dated Apr. 2, 2013.

International Search Report and Written Opinion corresponding to PCT/US2012/067741 dated Apr. 2, 2013.

International Search Report and Written Opinion received in Patent Cooperation Treaty Application No. PCT/US2013/026066, dated Apr. 17, 2013, 11 pages.

* cited by examiner

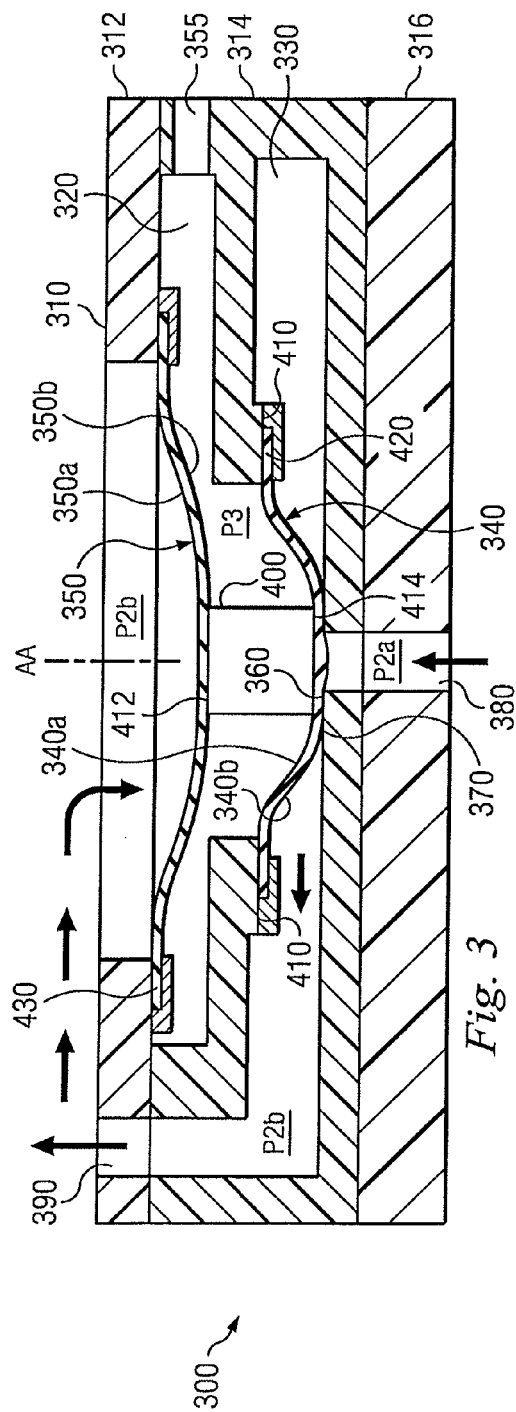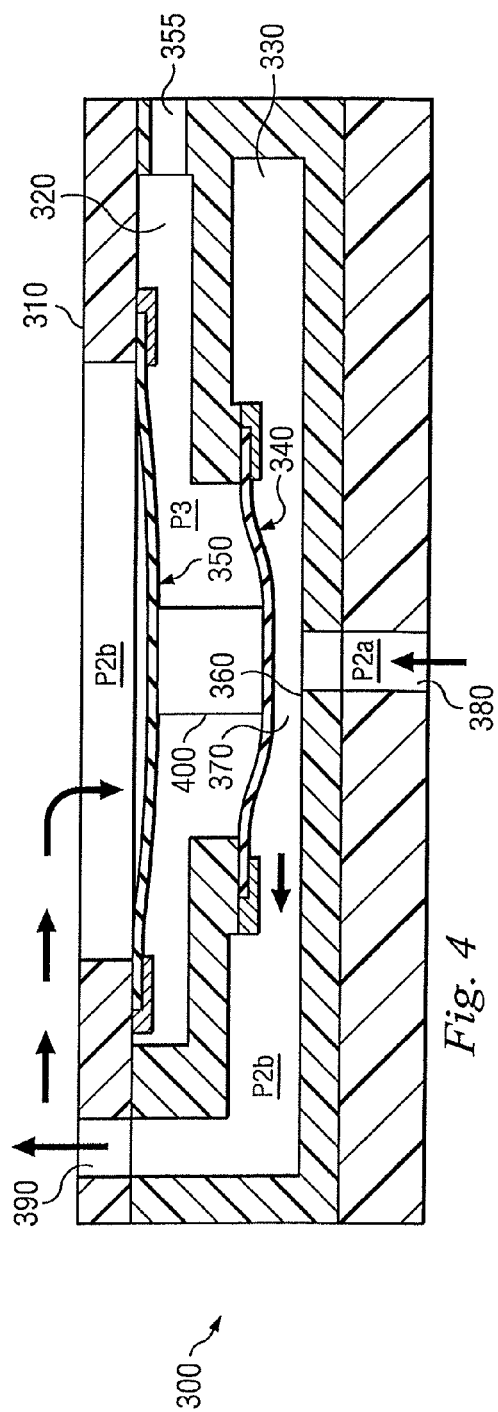

ACTIVE DRAINAGE SYSTEMS WITH DUAL-INPUT PRESSURE-DRIVEN VALVES

PRIORITY CLAIM

This application claims the benefit of priority of U.S. Patent Application Ser. No. 61/569,976 titled "ACTIVE DRAINAGE SYSTEMS WITH DUAL-INPUT PRESSURE-DRIVEN VALVES," filed on Dec. 13, 2011, whose inventor is Leslie A. Field, which is hereby incorporated by reference in its entirety as though fully and completely set forth herein.

BACKGROUND

The present disclosure relates generally to valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidly coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development of the bleb typically includes fibrosis, which leads to increased flow resistance and it is generally the case that this resistance increases overtime. This development and progression of fibrosis reduces or eliminates flow from the anterior chamber, eliminating the capacity of the drainage device to affect IOP.

Some examples of IOP control systems or implants protect against under-drainage while simultaneously guarding against over-drainage, and consequently reduce or eliminate bleb formation and fibrotic changes. The system and methods disclosed herein overcome one or more of the deficiencies of the prior art.

SUMMARY

In one exemplary aspect, the present disclosure is directed to a pressure-driven valve that comprises a housing and a flow control portion. The housing comprises a fluid inlet and a fluid outlet, and the flow control portion is disposed within the housing. The flow control portion has a first side subject to fluid flow pressure in a fluid flow channel, and has a second side subject to an outlet pressure representative of pressure at the fluid outlet. The flow control portion is deformable to increase and decrease flow through the fluid flow channel based on pressure differentials between the fluid flow pressure, a tube pressure, and the outlet pressure.

In some instances, the flow control portion further comprises a flow control membrane and a radially-fluctuating pressure tube attached to the periphery of the flow control membrane. The pressure tube comprises a hollow, flexible, curved tube including a closed end and an open end, and is curved to define a circular space having a first diameter. The pressure tube is filled with fluid conveying the tube pressure, and is deformable in response to pressure differentials between the outlet pressure and the tube pressure, thereby deforming the fluid flow membrane to increase and decrease flow through the fluid flow channel.

In another exemplary aspect, the present disclosure is directed to a pressure-driven valve for implantation in a patient. The pressure-driven valve comprises a housing, a fluid flow channel, a pressure tube disposed within the housing, and a deformable portion attached to the pressure tube. The housing comprises a fluid inlet and a fluid outlet, and the fluid flow channel extends between the fluid inlet and the fluid outlet. The pressure tube comprises a hollow, flexible, curved tube including a closed end and an open end, is filled with fluid conveying a tube pressure, and is curved to define a circular space having a first diameter. The deformable portion defines a portion of the fluid flow channel and is configured to deform to increase and decrease a size of the fluid flow channel to regulate fluid flow from the fluid inlet to the fluid outlet. The deformable portion is disposed and arranged to deform as a result of pressure differentials between the tube pressure, a fluid flow channel pressure, and an outlet pressure representative of fluid pressure at the fluid outlet.

In another exemplary aspect, the present disclosure is directed to an IOP control system for implantation in an eye of a patient. The system comprises a drainage tube and a pressure-driven valve system. The drainage tube is configured to convey aqueous humor from an anterior chamber of the eye, and the pressure-driven valve system is in fluid communication with the drainage tube. The valve system includes a first pressure-driven valve and a second pressure-driven valve, and is actuatable in response to pressure differentials and configured to control flow rates of the aqueous humor. The first pressure-driven valve is configured to control flow rates of the aqueous humor along the drainage tube by shifting in response to the pressure differential between the anterior chamber of the eye and the atmospheric pressure acting on the first valve. The second pressure-driven valve comprises a pressure tube attached to the periphery of a flow control membrane, and the pressure tube comprises a hollow, flexible, curved tube including a closed end and an open end. The pressure tube is filled with fluid conveying the atmospheric pressure. The second pressure-driven valve is configured to control flow rates of aqueous humor along the drainage tube by deforming in response to the pressure differentials between the atmospheric pressure, the pressure in the drainage tube between the first and second valves, and the pressure of the drainage site acting on the second valve.

In another exemplary aspect, the present disclosure is directed to a method of regulating IOP by adjusting drainage from an anterior chamber of an eye with a membrane valve. The method includes directing fluid through a fluid flow passageway extending between a fluid inlet and a fluid outlet within the membrane valve. The method also includes modifying the size of the fluid flow channel through deformation of a flow control membrane attached to a hollow, flexible, radially-fluctuating pressure tube as a result of pressure differentials between a tube pressure, a fluid flow channel pressure, and an outlet pressure representative of fluid pressure at the fluid outlet.

Providing actively responsive valves in the IOP control system that function even in the absence of an energy supply may reduce bleb formation and subsequent fibrotic changes, and thus significantly increase the functional life of the IOP control system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 3 is a schematic cross-sectional diagram of an exemplary pressure-driven valve in a closed condition according to one embodiment of the present disclosure.

FIG. 4 is a schematic cross-sectional diagram of the pressure-driven valve shown in FIG. 3 in an open condition according to one embodiment of the present disclosure.

DETAILED DESCRIPTION

Figure 1:
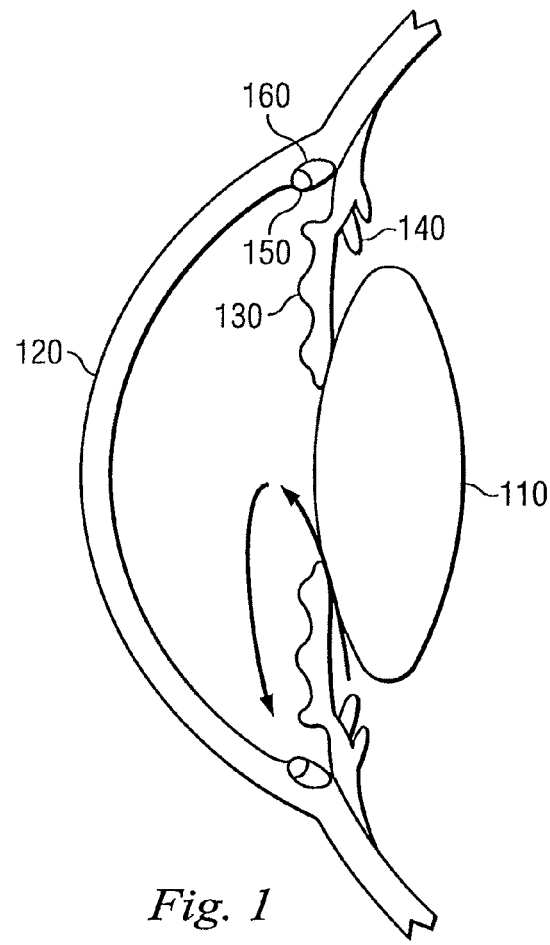
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

Figure 2:
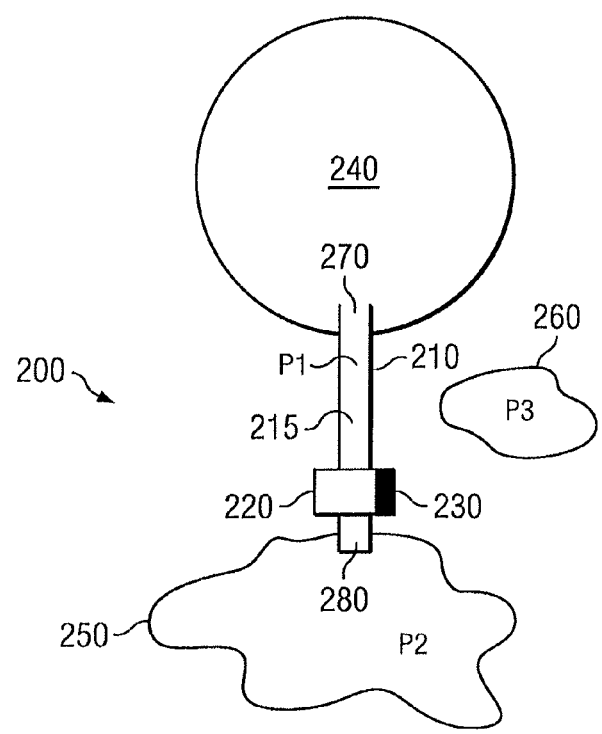
FIG. 2 is a schematic diagram of an exemplary IOP control system implanted in the eye according to one embodiment of the present disclosure.

FIG. 2 is a diagram of an exemplary IOP control system 200, including a drainage tube 210, a valve system 220, and a divider 230. The IOP control system 200 is positioned in the eye with one end 270 of the drainage tube 210 located in the anterior chamber 240 and the opposite end 280 located outside the anterior chamber 240 in a drainage site 250.

The IOP control system 200 may be positioned within the eye in the subconjunctival pocket between the conjunctiva and the sclera with the anterior border of the valve system 220 positioned approximately 8-10 millimeters posterior to the limbus (the border between the cornea and the sclera). The IOP control system 200 may be held in place within the eye via anchoring structures, the angle of implantation and surrounding anatomy, or by a spring force or other mechanisms that stabilize the IOP control system 200.

In the embodiment pictured in FIG. 2, three areas of pressure interact with the IOP sensor system 200: P1, P2, and P3. Pressure area P1 reflects the pressure of the anterior chamber 240, pressure area P2 reflects the pressure of the drainage site 250 in the subconjunctival space (and may reflect bleb pressure), and pressure area P3 reflects a reference pressure located remotely from P1 and P2 in a dry location 260 (effectively reflecting atmospheric pressure). In some embodiments, pressure area P1 reflects the pressure located in a lumen or tube that is in fluidic communication with the anterior chamber 240.

The IOP control system 200 responds to the pressure differentials between P1, P2, and P3 to control the valve system 220 and thereby control the flow rate of aqueous humor through drainage tube 210. More specifically, the various pressure differentials across pressure areas P1, P2, and P3 (P1–P2, P1–P3, P2–P3) drive the valve system 220 and dictate the flow rate of aqueous humor through the drainage tube 210 without requiring external power at the valve system 220.

The drainage tube 210 drains aqueous humor from the anterior chamber 240 of the eye. The valve system 220 controls the flow of aqueous humor through a lumen 215 of the tube 210. In the embodiment shown, the pressure area P1 reflects the pressure in the lumen 215 upstream from the valve system 220 and downstream from the anterior chamber 240. The expected discrepancy between the true anterior chamber pressure and that reflected by area P1 when located in a tube downstream of the anterior chamber 240 (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water. Therefore, because there is almost no pressure difference between the anterior chamber 240 and the interior of the tube 210 that is in fluid contact with the anterior chamber 240, pressure area P1 effectively reflects the pressure of the anterior chamber 240.

As shown in FIG. 2, the drainage tube 210 may be arranged to shunt fluid from the anterior chamber 240 to the drainage site 250, which may be at any of numerous locations within the eye. For example, some tubes 210 are arranged to shunt aqueous from the anterior chamber 240 to the subconjunctival space, thus forming a bleb under the conjunctiva, or, alternatively, to the subscleral space, thus forming a bleb under the sclera. Other tube designs shunt aqueous humor from the anterior chamber to the suprachoroidal space, the supraciliary space, the juxta-uveal space, or to the choroid, thus forming blebs in those respective locations. In other applications, the drainage tube 210 shunts aqueous humor from the anterior chamber 240 to Schlemm's canal, a collector channel in Schlemm's canal, or any of a number of different blood vessels like an episcleral vein. In some examples, the drainage tube 210 even shunts aqueous humor from the anterior chamber 240 to outside the conjunctiva. Each of these different anatomical locations to which aqueous humor is shunted is an example of a drainage site 250. Other examples of a drainage site 250 include, but are not limited to: a subconjunctival space, a suprachoroidal space, a subscleral space, a supraciliary space, Schlemm's canal, a collector channel, an episcleral vein, an uveo-scleral pathway, and other locations.

In some embodiments, a divider 230 separates pressure areas P1 and P2 from pressure area P3. Pressure area P2 reflects the pressure at a drainage site 250. As such, pressure area P2 may be located in a pocket, such as a bleb, that generally contains aqueous humor or in communication with such a pocket, via a tube, for example, and is in a wet location. Pressure area P3 is physically separated from both pressure area P1 and pressure area P2 by divider 230. Divider 230 is a physical structure that separates and isolates the pressure area P1 and the wet drainage site 250 of pressure area P2 from the dry location 260 of pressure area P3. In some embodiments, the divider 230 includes the physical components of the valve system 220, such as parts of a housing. Note that the divider 230 may take many forms, such as, but not limited to, a tube extending pressure area P3 to a remote site or a pocket away from and fluidly independent of the drainage site.

In some embodiments of the present disclosure, the atmospheric pressure area P3 reflects the pressure in an area in close proximity to the eye, and in one embodiment, the pressure area P3 may reflect the pressure in the eye under the conjunctiva. In such cases, pressure area P3 reflects a pressure that can be correlated with atmospheric pressure. Pressure area P3 may also reflect the pressure of a dry portion 260 of the subconjunctival space, separate and apart from the drainage site 250. Regardless of location, pressure area P3 is intended to reflect the reference atmospheric pressure in the vicinity of the eye or at the eye's surface.

Generally, IOP is a gauge pressure reading—the difference between the absolute pressure in the eye (as reflected by P1) and atmospheric pressure (as reflected by P3). Atmospheric pressure, typically about 760 mm Hg, often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mm Hg. Because the pressure area P3 reflects atmospheric pressure, the difference in pressure between the pressure areas P1 and P3 provides an indication of IOP (the pressure differential between the anterior chamber 240 and the atmospheric pressure). Thus, for accurate control of IOP, it is desirable to have an IOP control system reactive to the pressure differential across the pressure of the anterior chamber (as reflected by P1) and atmospheric pressure in the vicinity of the eye (as reflected by P3). Therefore, in one embodiment of the present disclosure, the IOP control system 200 reacts to the pressure differential across P1 and P3 continuously or nearly continuously so that the actual IOP (as P1–P3 or P1–f(P3)) can be responded to accordingly.

The valve system 220 is connected to the drainage tube 210 and controls the flow of aqueous humor through the lumen 215 of the tube 210 from the anterior chamber 240 to the drainage site 250. The valve system 220 is disposed along, and may form a part of, the drainage tube 210 between the end 270 in the anterior chamber 240 and end 280 at the drainage site 250. In some embodiments, the valve system 220 is disposed within the lumen 215 of the drainage tube 210 between the end 270 and the end 280. The valve system 220 is configured to control the flow of fluid through the drainage tube 210, and thereby control pressure in the eye, including the IOP. For example, when the IOP is high, the valve system 220 may operate to permit increased flow through the drainage tube 210, and when IOP is low, the valve system 220 may operate to decrease the flow through the drainage tube 210. In the embodiment pictured in FIG. 2, the valve system 220 is configured to be continuously responsive to various pressure differentials (P1–P3 and P2–P3) and control fluid flow to the drainage site 250.

While several complications may arise from elevated IOP, various complications may arise from excessively low IOP as well. For example, hypotony is a complication associated with surgeries that serve to shunt the aqueous humor from the anterior chamber 240 to a drainage site 250. Hypotony is a dangerous, rapid drop in IOP that can result in severe consequences, such as choroidal hemorrhage and choroidal detachment. Thus, it is desirable to control the rate of aqueous outflow from the anterior chamber 240 to the drainage site 250 not only to prevent under-drainage of aqueous humor, but also to prevent over-drainage and hypotony. The valve system 220 can respond to the pressure differentials between the pressure areas P1, P2, and P3 to control the flow rate through the drainage tube 210.

In an exemplary embodiment of the present disclosure, the pressure differential across pressure areas P2 and P3 can control valve system 220 so as to prevent the formation of a bleb or control the morphology of a bleb. One of the problems associated with implant surgery is bleb failure. A bleb can fail due to poor formation or fibrosis. The pressure in the bleb is one factor that determines bleb morphology. As explained above, too much pressure can cause a bleb to migrate to an undesirable location or can lead to fibrosis. The valve system 220 takes into account the pressure area P2 to control the bleb pressure. In one embodiment of the present disclosure, the difference between the pressure in the bleb (as reflected by P2) and atmospheric pressure (as reflected by P3) can be used to control valve system 220 to maintain a desirable bleb pressure. In another embodiment of the present disclosure, the valve system 220 uses at least one dual-input pressure-driven valve responding to the pressure differential not only between the fluid (P2) and a reference pressure (P3), but also the pressure differential between two different reference pressures within the valve system 220. In this manner, the IOP control system 200 of the present disclosure can also be used to properly maintain a bleb. One of ordinary skill in the art will recognize that the IOP control devices and systems disclosed herein may be modified for use in other applications utilizing pressure-driven membrane actuation.

The valve system 220 includes at least one pressure-driven membrane valve that does not require external power or feedback from electronic pressure sensors to operate. The valve is configured to allow or block aqueous humor flowing through the drainage tube 210 to the drainage site 250. In some embodiments, the valve is located downstream of a valve (or valves) that allows aqueous humor to flow from the anterior chamber 240 through the drainage tube 210 in response to pressure differentials between P1 and P3. Thus, in some examples, the valve is located as a downstream valve in a valve array connected in series. In some examples, the valve system 220 may be formed as a part of or utilized in a valve system such as those disclosed in related application Ser. No. 13/315,329 titled "Active Drainage Systems with Pressure-Driven Valves and Electronically-Driven Pump" incorporated herein by reference. The pressure-driven membrane valves disclosed herein may form the downstream valves of the valve system in the incorporated application, titled "Active Drainage Systems with Pressure-Driven Valves and Electronically-Driven Pump."

FIG. 3 illustrates a pressure-driven membrane valve 300 according to one embodiment of the present disclosure that includes a housing 310 that is defined by a housing section 312, a housing section 314, and a housing section 316, which mate with one another to form an enclosure within which various other components of the valve 300 are positioned. The housing 310 is divided into a reference chamber 320 and a fluid chamber 330. The reference chamber 320 is defined by the housing 310, a flow control membrane portion, such as membrane 340, a membrane 350, and a pressure access port 355. The fluid chamber 330 houses a valve seat 360, a fluid flow channel 370, a fluid inlet 380, and a fluid outlet 390. A biasing member 400 connects the flow control membrane 340 and the membrane 350. The fluid inlet 380, the flow control membrane 340, the biasing member 400, the membrane 350 are all centrally aligned about a central axis AA. In alternative embodiments, asymmetrical arrangements of the components of the valve are contemplated. In the pictured embodiment, the components of the valve 300, including the flow control membrane 340 and the membrane 350, are generally circular in geometry. In alternative embodiments, different geometries for the valve are contemplated, including ovoid and rectangular geometries, for example. In some embodiments, the housing sections are integrally formed.

In the pictured embodiment, the housing 310 is divided into the reference chamber 320 and the fluid chamber 330 by the flow control membrane 340 and a shelf 410 of the housing section 314. Here, the shelf 410 is generally shaped and configured to form an annular ring extending circumferentially from the inner wall of the housing section 314. The flow control membrane 340 is anchored to the shelf 410 in this embodiment, while other embodiments use other anchoring or adhesion methods. The housing section 316 forms the fluid inlet 380 and housing section 314 forms the valve seat 360 within the fluid chamber 330. The fluid inlet 380 fluidly connects the drainage tube 210 to the valve 300. The housing sections 312 and 314, and 316 cooperate to form the fluid outlet 390. The valve seat 360 is positioned between the fluid inlet 380 and the fluid outlet 390 such that fluid flows into the fluid inlet 380, through the fluid flow channel 370, and out the fluid outlet 390. In some embodiments, the entire housing is integrally formed. The housing 310 may be constructed of any suitable biocompatible material, provided the material is able to maintain constructional integrity at high internal pressures and withstand pressure changes.

The reference chamber 320 is bounded and defined by at least the housing sections 312, 314, the flow control membrane 340, the membrane 350, and the pressure access port 355. The reference chamber 320 may be in communication with pressure area P3, which is expected to reflect atmospheric pressure, through the pressure access port 355. In some embodiments, P3 reflects the pressure area of the (relatively) dry subconjunctival space. In alternative embodiments, a plurality of membranes using separate reference chambers (and reference chamber pressures) is contemplated for use in the valve 300.

In the embodiments shown, the valve seat 360 is a floor surface of the housing section 314. The central aperture of the valve seat 360 serves as the entrance to the fluid flow channel 370. The valve seat 360 is shaped and configured such that when the flow control membrane 340 rests on the valve seat 360, the valve 300 is in a closed condition. The valve seat 360 is positioned relative to the fluid inlet 380 such that the central apertures of the valve seat 360 and the fluid inlet 380 are co-aligned about the central axis AA. Thus, in the embodiment pictured in FIG. 3, the central aperture of the valve seat 360 serves as both the exit of the fluid inlet 380 and the entrance to the fluid flow channel 370, and when the flow control membrane 340 rests on the valve seat 360, the valve 300 is in a closed position.

In other embodiments, a boss member may be positioned on the valve seat 360 such that the boss member concentrically overlies the fluid inlet 380. In these embodiments, the boss member effectively functions as the valve seat. A boss member may permit increased design flexibility and flow control for the valve 300. Varying the height and other dimensions of the boss member could affect the amount and rate of fluid flow through the valve 300.

The fluid flow channel 370 comprises the circumferential gap that arises between the valve seat 360 and the flow control membrane 340 when the flow control membrane 340 lifts away from the valve seat 360 toward the reference chamber 320. As shown in FIG. 3, when the valve 300 is in a closed condition and the flow control membrane 340 rests on the valve seat 360, the fluid flow channel 370 is a potential space or gap. As shown in FIG. 4, the fluid flow channel 370 enlarges to an actual space or gap when the flow control membrane 340 lifts off the valve seat 360 and the valve 300 is in an open or partially open condition. When the valve 300 is in an open condition, the fluid flow channel 370 is generally a constant height around the annular sealing surface of the valve seat 360 (i.e., the gap between the valve seat 360 and the membrane 340 is generally uniform) at any given time.

Returning to FIG. 3, the biasing member 400 may be shaped and sized as a solid cylinder having two parallel circular faces 412, 414. The biasing member 400 extends between the flow control membrane 340 and the membrane 350. In the pictured embodiment, the biasing member 400 is sized to have a larger diameter than the diameter of the fluid inlet 380. The biasing member 400 fixedly attaches to both the membrane 350 and the flow control membrane 340 such that movement of the biasing member 400 in one direction causes the simultaneous movement of the membrane 350 and the flow control membrane 340 in the same direction. More specifically, the face 412 of the biasing member 400 attaches to the center of the membrane 350, and the face 414 of the biasing member 400 attaches to the center of the flow control membrane 340. In other embodiments, the biasing member may comprise any of a variety of three dimensional shapes, including cubic or polygonal, for example. In other embodiments, the biasing member 400 may be sized to have the equivalent diameter to or a smaller diameter than the fluid inlet 380. The shape of the biasing member 400 may be chosen depending upon spatial, pressure drop, material, and flow rate constraints.

The flow control membrane 340 comprises a flexible, deformable, fluid-tight membrane or diaphragm that provides valve functionality by deflecting in response to pressure differentials across its two opposing sides. The flow control membrane 340 includes two parallel sides, a side 340a and an opposite side 340b. The side 340a faces the reference chamber 320, and consequently conveys the pressure of pressure area P3, which may reflect atmospheric pressure. The side 340b faces the fluid chamber 330, and in particular the fluid inlet 380, and consequently conveys the pressure of pressure area P2a, which reflects the pressure of the fluid within lumen 215 of the drainage tube 210 located upstream of the valve 300. The side 340a of the flow control membrane 340 is coupled with the face 414 of the biasing member 400 such that movement of the biasing member 400 causes simultaneous and proportional movement of the flow control membrane 340 in the same direction as the biasing member 400. The side 340b of the flow control membrane 340 is configured to selectively seal against the valve seat 360 and thereby close the valve 300 when movement of the biasing member 400 is sufficient, which is driven by membrane 350, as explained below. Alternatively, the membrane 340 may move sufficiently to partially close the valve to restrict rather than cut off flow.

As shown in FIG. 3, the flow control membrane 340 is securely held in place within the housing 310 so that it will not be displaced by the force of the fluid flowing through the valve 300. In the embodiment pictured in FIG. 3, the flow control membrane 340 is anchored to the shelf 410 of the housing section 314. More specifically, a peripheral zone 420 of the flow control membrane 340 is connected to the underside of the shelf 410. The housing section 314 and the flow control membrane 340 are secured into this arrangement by any of a variety of known methods, including adhesive, welding, or mechanical fasteners, for example. In some embodiments, the movable membrane can be fabricated integrally with some or all of the housing features by micromachining or MEMS techniques as are well known in the art using a series of material deposition, lithographic patterning and etching steps on suitable substrates. As an example, a suitable substrate may use a Si or glass wafer as a starting point, with various spacing layers of Silicon, glass, dielectric, or spin-on materials to form parts of the housing, and a flexible membrane material such as thinned silicon, silicon nitride, compliant metal such as gold, or biocompatible organic materials such as Parylene, silicone rubber, PDMS or the like, alone or in combination, in suitable thicknesses and dimensions to yield the desired performance.

In various other embodiments, the flow control membrane 340 may be anchored anywhere within the housing 310 to separate the housing 310 into two distinct chambers, a reference chamber and a fluid chamber. For example, some embodiments lack the shelf 410, and the flow control membrane is anchored directly to the housing 310. Regardless of how the flow control membrane 340 is secured within the housing 310, at least a portion of the housing 310 is connected to a periphery of the flow control membrane 340 to maintain it in a desired position relative to the valve seat 360.

The membrane 350 comprises a flexible, deformable, fluid-tight membrane or diaphragm that provides valve functionality by deflecting in response to pressure differentials across its two opposing sides. The membrane 350 is sized to have a diameter significantly larger than the diameter of the flow control membrane 340. The membrane 350 includes two parallel sides, a side 350a and an opposite side 350b. The side 350a faces the drainage site 250 downstream of the valve 300, and consequently conveys the pressure of pressure area P2b, which reflects the pressure of the fluid at drainage site 250 located downstream of the valve 300. The side 350b faces the reference chamber 320, and consequently conveys the pressure of pressure area P3, which may reflect atmospheric pressure. The side 350b of the membrane 350 is coupled with the face 412 of the biasing member 400 such that movement of the membrane 350 causes simultaneous and proportional movement of the flow control membrane 340 in the same direction as the biasing member 400, and visa-versa. As will be explained in further detail below, the membrane 350 shifts in response to pressure differences between drainage site 250 (downstream of the valve 300) and the reference chamber 320 to dominate and control the movement of the biasing member 400, which influences the open and closed condition of the valve 300.

The membrane 350 is securely held in place within the housing 310 so that it will not be displaced by the force of the pressure differentials acting on the valve 300. In the embodiment pictured in FIG. 3, the membrane 350 is anchored to the housing section 312. More specifically, a peripheral zone 430 of the membrane 350 is connected to the underside of the housing section 312. The housing section 312 and the membrane 350 are secured into this arrangement by any of a variety of known methods, including adhesive, welding, or mechanical fasteners, for example. The movable membranes 350 and 340 can be fabricated integrally with some or all of the housing features by micromachining or MEMS techniques as are well known in the art using a series of material deposition, lithographic patterning and etching steps on suitable substrates. As an example, a suitable substrate may use a Si or glass wafer as a starting point, with various spacing layers of Silicon, glass, dielectric, or spin-on materials to form parts of the housing, and a flexible membrane material such as thinned silicon, silicon nitride, compliant metal such as gold, or biocompatible organic materials such as Parylene, silicone rubber, PDMS or the like, alone or in combination, in suitable thicknesses and dimensions to yield the desired performance. In other embodiments, the membrane 350 may be anchored to anywhere on the housing 310 provided the membrane 350 separates the reference chamber 320 from the drainage site 250 (downstream of fluid flow channel 370). Regardless of how the membrane 350 is secured on the housing 310, at least a portion of the housing 310 is connected to a periphery of the membrane 350 to maintain it in a desired position relative to the flow control membrane 340.

In the pictured embodiment, the flow control membrane 340 and the membrane 350 are shaped and configured as substantially planar membranes having a circular shape. Other shapes are also contemplated for the membranes 340, 350, including, but not by way of limitation, rectangular or ovoid shapes. The shape of the membranes 340, 350 may be chosen depending upon spatial, pressure drop, material, and flow rate constraints.

For purposes of practicality, the membranes 340, 350 should be thick enough to be durable and resistant to corrosion and leakage. However, the membranes 340, 350 should also be thin enough to provide the necessary flexibility and deflection capabilities which are required in a substantially planar membrane designed for use in a pressure-responsive IOP control system 200. A preferred thickness of the flow control membrane 340 will depend on the deflection response desired for a given pressure and the material chosen. As an example, it may be fabricated out of Parylene and may have a thickness ranging from 0.5 µm to 30 µm. The membrane 350 may have a similar thickness and material as membrane 340, or for the sake of illustrating a different favorable choice, it could be made of Silicon and have a thickness ranging from 0.3 µm to 10 µm. In some embodiments, the membrane includes annular corrugations. The thickness, material, and diameter of the membranes 340, 350, as well as the depth, number, and orientation of the corrugations, may all affect the cracking pressure of the flow control membrane 340.

The valve 300 is configured as a flow control valve that can completely or partially block the flow of aqueous humor by deflecting the flow control membrane 340 completely or partially across the fluid inlet 380. The housing 310 is configured to connect with drainage tube 210 such that deflection of the flow control membrane 340 at least partially opens and closes the lumen 215 to the outflow of aqueous humor. As described above, the position of the flow control membrane 340 relative to the valve seat 360 determines whether the valve 300 is in an open or closed condition. When the membrane 340 seals against the valve seat 360, the valve 300 is in a closed condition. When the membrane 340 deflects away from the valve seat 360, the valve 300 is in an open condition.

The valve 300 is in fluidic communication with the drainage tube 210 and in communication with P3, which reflects the atmospheric pressure (typically at the relatively dry subconjunctiva). In particular, the fluid inlet 380 fluidly interfaces with the drainage tube 210 proximal to the valve 300 (reflecting pressure area P2a), the membrane 350 interfaces with the drainage site 250 distal the valve 300 (reflecting pressure area P2b), and the reference chamber 320 interfaces with the dry subconjunctiva (reflecting pressure area P3). The flow control membrane 340 extends across the housing 310 to form a sealed separation between the reference chamber 320 and the fluid inlet 380, thereby creating an effective separation between pressure areas P3 and P2a, respectively. Accordingly, as the pressure increases against one side of the flow control membrane 340, the pressure increase acts to displace the flow control membrane 340 and the biasing member 400 in the direction away from the higher pressure. The fluid inlet 380 conveys the pressure of pressure area P2a on one side 340b of the flow control membrane 340. The reference chamber 320 conveys the pressure of pressure area P3 on the opposite side 340a of the flow control membrane 340.

Similarly, the membrane 350 extends across the housing 310 to form a sealed separation between the reference chamber 320 and the drainage site 250 distal to the valve 300, thereby creating an effective separation between pressure areas P3 and P2b, respectively. Accordingly, as the pressure increases against one side of the membrane 350, the pressure increase acts to displace the membrane 350 and the biasing member 400 in the direction away from the higher pressure. The fluid within the drainage site 250 distal to the valve 300 conveys the pressure of pressure area P2b on one side 350a of the membrane 350. The reference chamber 320 conveys the pressure of pressure area P3 on the opposite side 350b of the membrane 350.

Thus, the valve 300 provides a dual membrane response to pressure differentials at least in part because of the attached configuration of the biasing member 400, the membrane 350, and the flow control membrane 340. The flow control membrane 340 shifts within the housing 310 in response to the pressure differential between P2a and P3, and the membrane 350 shifts in response to the pressure differential between P2b and P3. In particular, and as stated above, the flow control membrane 340 deflects within the housing 310 of the valve 300 in response to the pressure differential between the fluid inlet 380 pressure (P2a) against one side 340b of the flow control membrane 340 and the relatively dry subconjunctival pressure (P3) against the opposite side 340a of the flow control membrane 340. With respect to the membrane 350, the membrane 350 deflects within the housing 310 in response to the pressure differential between the drainage tube pressure distal to the valve outlet 390 (P2b) against one side 350a of the membrane 350 and the reference chamber pressure (P3) against the opposite side 350b of the membrane 350.

The movement of either of the pressure-driven membranes 340, 350 in one direction causes the simultaneous movement of the biasing member 400, which moves in the same direction as the moving pressure-driven membrane. In the pictured embodiment, the membrane 350 dominates and controls the movement of the biasing member 400 because the membrane 350 has a significantly larger diameter and surface area than the flow control membrane 340. That is, because force is equivalent to pressure multiplied by area (F=P×A), the net force on the biasing member 400 may be calculated as follows (ignoring the thickness of the biasing member for the sake of simplicity):

$$F{net}_{Biasing\ member} = ((P2b-P3) \times A_{upper\ membrane}) - ((P2a-P3) \times A_{lower\ membrane})).$$

Thus, the biasing member 400 is mostly driven by the force exerted by the membrane 350, which has a larger surface area than the flow control membrane 340. Consequently, the P2b:P3 pressure differential across the membrane 350 controls the valve 300 more than the P2a:P3 pressure differential across the flow control membrane 340.

The cracking pressure of a valve generally refers to the minimum pressure differential needed between the inlet and outlet of the valve to lift the membrane off its seat. The cracking pressure of the valve 300 is dependent upon both the P2a:P3 pressure differential across the flow control membrane 340 and the P2b:P3 differential across the membrane 350, though for the embodiment shown in FIG. 3 the latter differential dominates the open/closed condition of valve 300 and thus its cracking pressure. If the pressure distal the valve outlet 390 (P2b) is too high in comparison to the atmospheric pressure (P3), the membrane 350 will deflect toward the reference chamber 320 and push the biasing member 400 toward the valve seat 360, which pushes the flow control membrane 340 against the valve seat 360 and stops flow through the valve 300. Because the larger membrane 350 exerts a greater force upon the biasing member 400 than the smaller flow control membrane 340, the valve 300 will remain in a closed condition in such a situation even if the pressure of the incoming fluid (P2a) is higher by the same amount in comparison to the atmospheric pressure (P3). That is, even if the pressure differential across the flow control membrane 340 is the same as the pressure differential across the membrane 350, the valve 300 will remain closed if the pressure of the drainage site (P2b) is too high in comparison to the atmospheric pressure (P3). This configuration allows the valve 300 to assume a closed condition if the pressure (P2b) at the drainage site 250, which may be within a bleb, becomes too high with respect to the atmospheric pressure (P3), reflecting an over-drainage situation. Conversely, this configuration allows the valve 300 to assume an open position if the pressure (P2b) at the drainage site is low enough with respect to atmospheric pressure (P3) to permit drainage.

The cracking pressure of the valve 300 is dependent mainly upon the force exerted by the membrane 350 on the biasing member 400, but is also influenced by the characteristics of the flow control membrane 340. Therefore, the cracking pressure of the valve 300 is dependent upon the type, diameter, and stiffness of the flow control membrane 340, the type, diameter, and stiffness of the membrane 350, the size and shape of the biasing member 400, and the nature of the connection between the biasing member 400 and the membranes 340, 350. Accordingly, the cracking pressure may be preselected by controlling these parameters during the manufacturing or assembly processes. In addition, the surgeon may select a valve 300 having a particular cracking pressure based on the most appropriate or desired IOP range for the treatment of a particular condition.

FIG. 3 illustrates the valve 300 in a closed, flow-blocking position. In the situation depicted in FIG. 3, the valve 300 is in a closed position because the pressure differential (P2b–P3) across the membrane 350 is high enough to push the flow control membrane 340 against the valve seat 360 and because the pressure differential (P2a–P3) across the flow control membrane 340 is not exceedingly high. The flow control membrane 340 rests on the sealing surface of the valve seat 360, thereby blocking the flow of aqueous humor from the fluid inlet 380, through the fluid flow channel 370, into the fluid outlet 390, and through the drainage site 250. The valve system 220 is self-limiting because the pressure-driven valve 300 will not open to allow aqueous humor to drain into the drainage site 250 unless the pressure differential across the valve 300 overcomes the cracking pressure of the valve 300 or unless the pressure differential (P2a–P3) across the flow control membrane 340 is exceedingly high.

FIG. 4 illustrates the valve 300 in an open, flow-permitting condition. At least in part because the pressure differential (P2b–P3) across the membrane 350 is not high enough to cause the membrane 350 to push the biasing member 400 toward the fluid inlet 380, the flow control membrane 340 rises off the valve seat 360 and the valve 300 assumes an open condition, thereby allowing aqueous humor to flow through the fluid flow channel 370 from the fluid inlet 380 to the fluid outlet 390 in the direction of any remaining valves and the drainage site 250. As shown in FIG. 4, a second necessary condition for the valve 300 to be in an open, flow-permitting condition is that the pressure differential (P2a–P3) across the flow control membrane 340 not be exceedingly negative, a state which is highly unexpected in the embodiment presented. This ensures that drainage of the aqueous humor occurs through the drainage tube 210 if the drainage site pressure (P2b) is within a desirable range (with respect to atmospheric pressure).

In addition, in some embodiments, the flexural resistance of the flow control membrane 340, which is lifted off valve seat 360 in the unpressurized case (i.e., when P2b=P3=P2a), increases with greater displacement. Accordingly, in higher pressure situations (referring to P2b–P3), the valve 300 will assume a more closed condition than in lower pressure situations. The higher the pressure of the fluid within the fluid outlet 390 (P2b) in comparison with the pressure of the reference chamber (P3), and assuming the P2a:P3 pressure differential across the flow control membrane 340 is not exceedingly high, the more the flow control membrane 340 deflects, thereby reducing the entrance to and the dimensions of the fluid flow channel 370 and allowing smaller amounts of aqueous humor to flow from the fluid inlet 380, across the valve seat 360, and through the fluid outlet 390. Conversely, the lower the pressure of the fluid within the fluid outlet 390 (P2b) in comparison with the pressure of the reference chamber (P3), and assuming the P2a:P3 pressure differential across the membrane 340 is not exceedingly negative, the less the flow control membrane 340 deforms to block the entrance to the fluid flow channel 370, thereby permitting aqueous humor to enter the fluid flow channel 370.

In another embodiment, the flow control membrane 340 is mechanically relaxed in all positions of the biasing member 400. Thus, in such embodiments, the flow control membrane 340 mainly serves to separate the reference chamber 320 and the fluid chamber 330 and the resistance of motion of biasing member 400 is caused by mechanical tensioning of membrane 350 only. These embodiments create a system that more readily responds to the difference between P2b and P3 and is less sensitive to the difference between P2a and P3.

Figure 5:
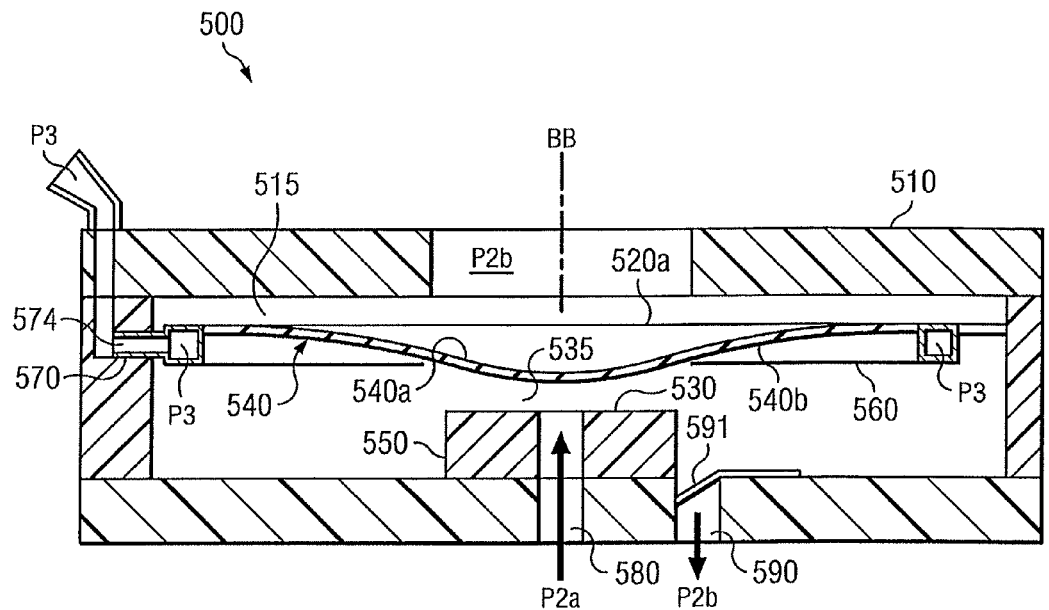
FIG. 5 is a schematic cross-sectional diagram of another exemplary pressure-driven valve in an open condition according to one embodiment of the present disclosure.

FIG. 5 illustrates a pressure-driven membrane valve 500 according to another embodiment of the present disclosure. The valve 500 does not require external power or feedback from electronic pressure sensors to operate. The valve 500 is configured to allow or block aqueous humor flowing from the anterior chamber 240 through the drainage tube 210 to any subsequent valves within the valve system 220 or to the drainage site 250. In the embodiment shown in FIG. 5, the pressure-driven membrane valve 500 includes a housing 510, reference chamber 515, a reference pressure tube 520a, a reference pressure tube 520b (not shown in FIG. 5), a valve seat 530, a fluid flow channel 535, a flow control membrane 540, and a boss member 550. In the pictured embodiment, the components of the valve 300 are generally circular in geometry and are generally symmetric about the center line BB. In alternative embodiments, different geometries for the valve are contemplated, including ovoid and rectangular geometries, for example. In alternative embodiments, the valve 500 includes any number of reference pressure tubes. For example, in some embodiments, the valve 500 includes only one reference pressure tube.

Figure 6:
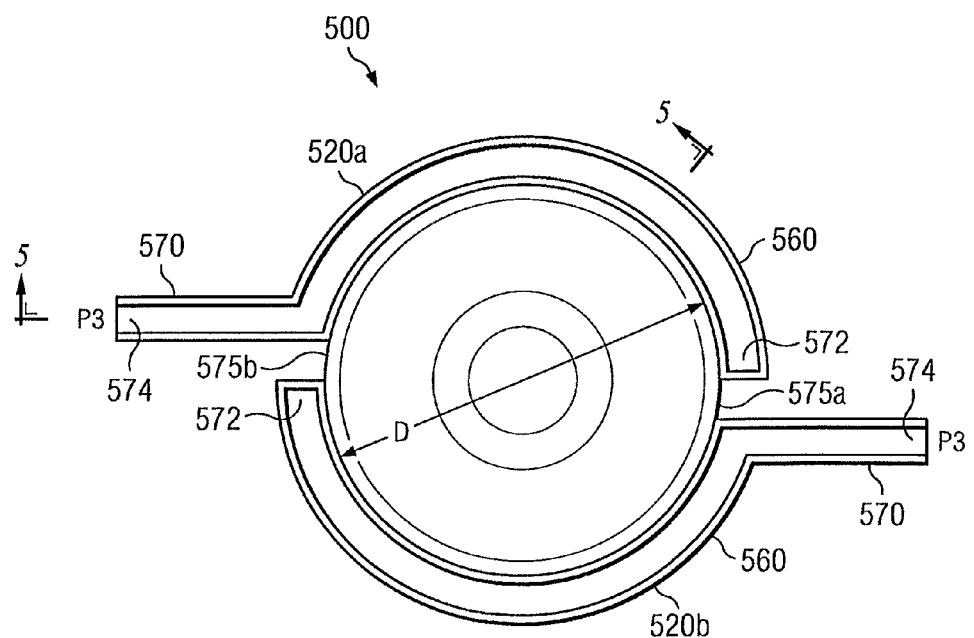
FIG. 6 is a top plan view of an exemplary flow control membrane and exemplary pressure tubes useable in the exemplary pressure-driven valve shown in FIG. 5 according to one embodiment of the present disclosure.

FIG. 6 illustrates a middle view of a portion of a pressure-driven membrane valve 500, showing the interconnection of the reference pressure tube 520a, the reference pressure tube 520b, and the flow control membrane 540. In the pictured embodiment, the flow control membrane 540 is shaped and configured as a substantially planar membrane having a circular shape with a diameter. Other shapes are also contemplated for the membrane 540, including, but not by way of limitation, rectangular or ovoid shapes. The shape of the flow control membrane 540 may be chosen depending upon spatial, pressure drop, material, and flow rate constraints. The flow control membrane 540 is securely held in place between the tubes 520a, 520b so that it will not be displaced by the force of the fluid flowing through the valve 500.

In the pictured embodiment, the tubes 520a, 520b are shaped and configured as flexible, hollow tubes having a C-shaped portion 560 and a linear tail portion 570. The C-shaped portion 560 terminates in a closed end 572, and the linear tail portion terminates in an open end 574. Other shapes are also contemplated for the tubes 520a, 520b, including, but not by way of limitation, rectangular or ovoid shapes. The shape of the tubes 520a, 520b may be chosen to echo the outer shape of the flow control membrane 540. In the pictured embodiment, the tubes 520a, 520b attach to the periphery of the flow control membrane 540 to form a circular configuration having an inner diameter D. The diameter of the flow control membrane 540 may be larger than the diameter D of the circular configuration of the tubes 520a, 520b such that the center of the membrane 540 droops to a lower plane than the tubes 520a, 520b when at rest. The flow control membrane 540 is circumferentially attached at its periphery to the tubes 520a, 520b such that deformation of either of the tubes 520a, 520b, whether pressure-induced or otherwise, causes simultaneous deformation of the flow control membrane 540. The flow control membrane 540 may be attached to the tubes 520a, 520b by any of a variety of known methods, including, but not by way of limitation, welding, adhesive, and mechanical fasteners, and as part of a micromechanical or MEMS fabrication sequence. In the pictured embodiment, only two small portions 575a, 575b of the periphery of the membrane 540 are not attached to either of the tubes 520a, 520b. Other embodiments may lack the portions 575a, 575b, or may possess smaller or larger portions 575a, 575b. The flow control membrane 540 and the tubes 520a, 520b will be more fully described below in relation to FIG. 5.

Returning to FIG. 5, FIG. 5 depicts a cross-sectional view of the valve 500 taken along lines 5-5 in FIG. 6, showing the larger environment of the flow control membrane 540 and the tube 520a. The housing 510 forms an enclosure within which various other components of the valve 500, such as the flow control membrane 540, the valve seat 530, and the boss member 550, are positioned. The housing 510 includes a reference chamber 515, a fluid inlet 580, a fluid outlet 590, and the valve seat 530. In various embodiments, the valve seat can have a separate narrow raised area or can be part of the boss structure as shown. The valve seat 530 is positioned between the fluid inlet 580 and the fluid outlet 590 such that fluid flows from the fluid inlet 580, through the fluid flow channel 535, and to the fluid outlet 590. A movable or deformable flap-valve or cantilever 591 may be present within or adjacent to the fluid outlet 590 to prevent backflow into the valve 500. In alternative embodiments, the housing 510 may be formed of separate sections that cooperate to anchor the flow control membrane 540 and the tubes 520a, 520b within the housing 510 and to form the fluid inlet 580 and the fluid outlet 590. The housing 510 may be constructed of any suitable biocompatible material, provided the material is able to maintain constructional integrity at high internal pressures and withstand pressure changes.

The reference chamber 515 is bounded and defined by at least the housing 510, the flow control membrane 540, and the tubes 520a, 520b. The reference chamber 515 is in communication with pressure area P2b, which reflects the fluid pressure of the drainage site 250. In some embodiments, the reference chamber 515 is in communication with the drainage site 250 directly.

In some embodiments, the valve seat 530 may be a floor surface of the housing 510. In the pictured embodiment, the boss member 550 is positioned on the valve seat 530 such that the boss member concentrically overlies the fluid inlet 580. It should be noted that some contemplated embodiments do not include the boss member 550. In a valve without a boss member, the central aperture of the valve seat 530 serves as the entrance to the fluid flow channel 535. In a valve without a boss member, the valve seat is shaped and configured such that when the flow control membrane 540 rests on the valve seat 530, the valve 500 is in a closed condition. In some embodiments, the valve seat can be a specific raised area, not shown here.

In the pictured embodiment in FIG. 5, the valve 500 includes a boss member 550 shaped and configured as a generally annular or toroid component. The boss member 550 is shaped and configured such that when the flow control membrane 540 rests on the boss member 550, the valve 500 is in a closed condition. The boss member 550 is positioned over the valve seat 530 such that the central apertures of the boss member 550 and the valve seat 530 are co-aligned about the central axis BB. The boss member 550 is positioned on the valve seat 530 such that the boss member 550 effectively functions as the valve seat, albeit at a raised position within the housing 500. Thus, in the embodiment pictured in FIG. 5, the central aperture of the boss member 550 serves as both the exit of the fluid inlet 580 and the entrance to the fluid flow channel 535, and when the flow control membrane 540 rests on the boss member 550, the valve 500 is in a closed position. The boss member 550 can permit increased design flexibility and flow control for the valve 500. Varying the height and other dimensions of the boss member 550 affects the amount and rate of fluid flow through the valve 500. In various embodiments, the boss member 550 may be configured as an integral extension of the valve seat 530, or may be a separate component. In some examples, the boss member 550 is an integral portion of the valve seat 530 and may be molded or machined at the same time as the valve seat 530. For example, the boss member may be fabricated by micromachining or MEMS techniques at the same time, or in processing steps before or after the fabrication of the valve seat feature, depending on the exact nature of the fabrication process used (such as whether the process steps used for these features are primarily additive or subtractive in nature).

Figure 7:
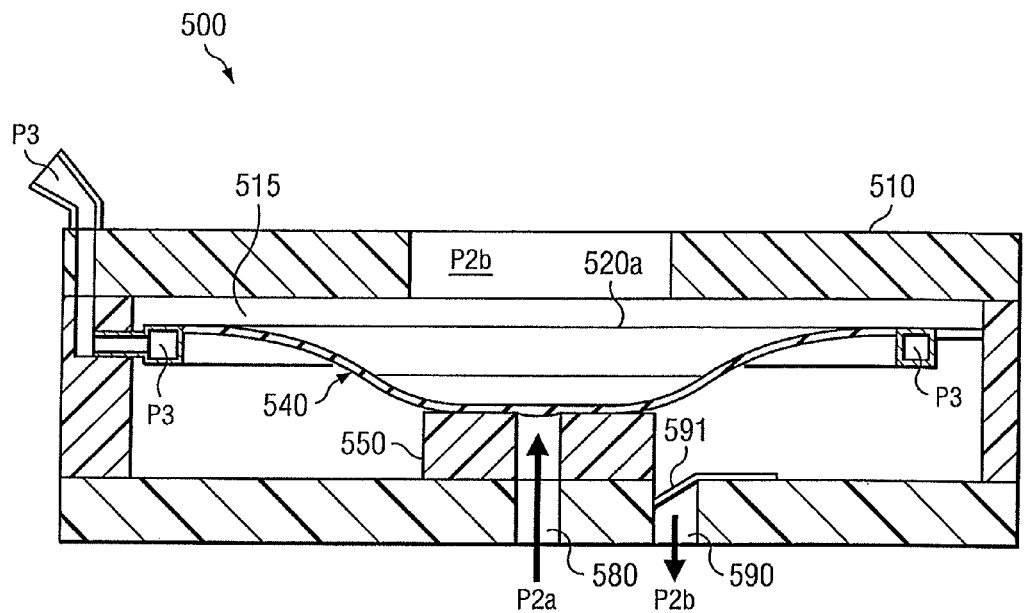
FIG. 7 is a schematic cross-sectional diagram of the exemplary pressure-driven valve shown in FIG. 5 in a closed condition according to one embodiment of the present disclosure.

The fluid flow channel 535 comprises the circumferential gap that arises between the boss member 550 (or, in embodiments without a boss member, valve seat 530) and the flow control membrane 540 when the flow control membrane 540 deflects away from the boss member 550 toward the reference chamber 520a. The fluid flow channel 535 is a potential space or gap when the flow control membrane 540 rests on the boss member 550 and the valve 500 is in a closed condition, as shown in FIG. 7. As shown in FIG. 4, however, the fluid flow channel 535 enlarges when the flow control membrane deflects off the boss member 550 into the reference chamber 515 and the valve 500 is in an open condition. When the valve 500 is in an open condition, the fluid flow channel 535 is generally a constant width around the annular sealing surface of the boss member 550 (i.e., the gap between the boss member 550 and the membrane 540 is generally uniform) at any given time.

The flow control membrane 540 comprises a flexible, deformable, fluid-tight membrane or diaphragm that provides valve functionality by (1) deflecting in response to pressure differentials across its two opposing sides, and (2) deforming in response to the pressure-induced flexion and extension of the tubes 520a, 520b. The flow control membrane 540 includes two parallel sides, a side 540a and an opposite side 540b. The side 540a faces the reference chamber 515, and consequently conveys the pressure of pressure area P2b. The side 540b faces the drainage tube 210 proximal to the valve 500, and in particular the fluid inlet 580, and consequently conveys the pressure of pressure area P2a. The side 540b of the flow control membrane 540 is configured to selectively seal against the boss member 550 and thereby close the valve 500 when the pressure against the side 540a sufficiently outweighs the pressure against the side 540b. As will be explained in further detail below, the flow control membrane 540 (1) deflects in response to pressure differences between pressure areas P2*a* and P2*b* and (2) deforms in response to the flexion and extension of the tubes 520*a*, 520*b* to at least partially open and close the valve 500 by changing the dimensions of the fluid flow channel 535. In some cases this latter effect should dominate the response of the valve to pressure differentials.

For purposes of practicality, the flow control membrane 540 should be thick enough to be durable and resistant to corrosion and leakage. However, the membrane 540 should also be thin enough to provide the necessary flexibility and deflection capabilities which are required in a substantially planar membrane designed for use in a pressure-responsive IOP control system 200. A preferred thickness of the flow control membrane 540 will depend on the deflection response desired for a given pressure and the material chosen. As an example, the membrane may be fabricated out of Parylene and have a thickness ranging from 0.5 µm to 30 µm. As another example, the membrane may be made of Silicon and have a thickness ranging from 0.3 µm to 10 µm. Note that these materials and thickness ranges are not intended to be exclusive. In some embodiments, the membrane includes annular corrugations. Membrane thickness, material, and diameter, in combination with the number, placement, and depth of the corrugations, all affect the cracking pressure of the valve 500.

The reference pressure tubes 520*a*, 520*b* are configured as Bourdon-style tubes. The Bourdon tube uses the principle that a flattened tube tends to change to a more circular cross-section when pressurized, and the strain on the material of the tube is magnified by forming the tube into a C-shape, such that the entire tube tends to straighten out or extend, elastically, as it is pressurized. In most Bourdon tubes, the tube possesses an open end and a closed end. The open end of the tube is connected to a fluid pressure source and the closed end of the tube is employed to shift an actuating arm or indicating arm in a circular path. Bourdon tubes respond to an increase in the fluid pressure within the tube by extending, which results in the closed end of the tube moving in a generally circumferential path which is translated into the rotational or linear movement of the actuating or indicating arm that may be referred to as radially-fluctuating. In the present disclosure, each tube 520*a*, 520*b* is substantially identical and incorporates the unique features of this disclosure. For simplicity of description, only one of the tubes (520*a*) will be described in detail and it should be understood that the tubes 520*a* and 520*b* act identically and in unison.

The reference pressure tubes 520*a*, 520*b* are anchored to the housing 510 such that the flow control membrane 540, which is attached to and suspended between the tubes 520*a*, 520*b*, may deflect in opposite directions toward and away from the fluid inlet 580 within the housing 510. The tubes 520*a*, 520*b* may be anchored within the housing 510 in any of a variety of known methods, provided the anchoring method does not interfere with the pressure-induced flexion or extension of the C-shaped portion 560. As mentioned above with reference to FIG. 6, the tube 520*a* comprises a hollow, flexible, curvilinear tube that is shaped and configured to include the curved, C-shaped portion 560 and the linear tail portion 570. The C-shaped portion 560 is fixedly attached to the periphery of the flow control membrane 540 such that pressure-induced deformation of the tube 520*a* causes simultaneous deformation of the flow control membrane 540. The linear tail portion 570 of tube 520*a* extends through the housing 510 such that the open end 574 is in communication with pressure area P3, which is expected to reflect atmospheric pressure. Thus, the fluid within the tube 520*a* conveys the pressure of pressure area P3 along the length of the tube 520*a*. In some embodiments, the tube 520*a* is in communication with the dry subconjunctiva. In alternative embodiments, the tube 520*a* interfaces with another portion of the eye or to atmospheric pressure directly.

The valve 500 is configured as a flow control valve that can completely or partially block the flow of aqueous humor by deflecting the flow control membrane 540 completely or partially across the fluid inlet 580. The housing 510 is configured to connect with drainage tube 210 such that deflection of the flow control membrane 540 at least partially opens and closes the lumen 215 to the outflow of aqueous humor. As described above, the position of the flow control membrane 540 determines whether the valve 500 is in an open or closed condition. When the membrane 540 seals against the boss member 550 or an alternative valve seat feature (only one exemplary valve seat shown), the valve 500 is in a closed condition. When the membrane 540 deflects away from the boss member 550, the valve 500 is in an open condition. The flow control membrane 540 controls the passage of aqueous humor through the valve 500 by (1) deflecting in response to pressure differences between pressure areas P2*a* and P2*b* and (2) deforming in response to the flexion and extension of the tubes 520*a*, 520*b* to at least partially open and close the valve 500 by changing the dimensions of the fluid flow channel 535.

The flow control membrane 540 controls the passage of aqueous humor through the valve 500 in part by deflecting in response to pressure differences between pressure areas P2*a* and P2*b* to at least partially open and close the valve 500 by changing the dimensions of the fluid flow channel 535. In particular, the fluid inlet 580 fluidly interfaces with the drainage tube 210 proximal the valve 500 (reflecting pressure area P2*a*) and the reference chamber 515 interfaces with the drainage site 250 distal the valve outlet 590 (reflecting pressure area P2*b*). The fluid inlet 580 conveys the pressure of pressure area P2*a* on one side 540*b* of the flow control membrane 540. The reference chamber 515 conveys the pressure of pressure area P2*b* on the opposite side 540*a* of the flow control membrane 540. The flow control membrane 540 and the tubes 520*a*, 520*b* extend across the housing 510 to form a sealed separation between the reference chamber 515 and the fluid inlet 580, thereby creating an effective separation between pressure areas P2*b* and P2*a*, respectively. Accordingly, as the pressure increases against one side of the flow control membrane 540, the pressure increase attempts to displace the flow control membrane 540 in the direction away from the higher pressure. However, as will be explained below, the design intent of valve 500 is such that the size of fluid flow channel 535 is relatively insensitive to the pressure differential across the membrane.

The flow control membrane 540 controls the passage of aqueous humor through the valve 500 in part by deforming in response to the flexion and extension of the tubes 520*a*, 520*b* to at least partially open and close the valve 500 by changing the dimensions of the fluid flow channel 535. In particular, the C-shaped portion 560 of the tube 520*a* flexes and extends in response to changing pressure differentials between the fluid pressure within the tube 520*a* (P3) and the pressure outside the tube 520*a* (P2*b*). When the pressure within the tube 520*a* (P3) sufficiently outweighs the pressure outside the tube (P2*b*), the closed end 574 of the tube 520*a* extends or attempts to uncoil, thereby pulling on the membrane 540 and causing it to stretch and lift off the boss member 550, which allows fluid to flow from the fluid inlet 580 through the valve 500. Conversely, when the pressure outside the tube 520*a* (P2*b*) is relatively high in comparison to the pressure within the tube 520a (P3), the closed end of the tube 520a flexes or attempts to coil up, thereby relieving the strain on the membrane 540 and allowing its center to sag onto the boss member 550, which prevents fluid from flowing into the valve 500.

In the situation depicted in FIG. 5, the valve 500 is shown in an open, flow-permitting condition. The flow control membrane 540 is lifted off the sealing surface of the boss member 550, thereby allowing the flow of aqueous humor from the fluid inlet 580 to the fluid outlet 590 and through the drainage site 250. A valve 500 having this configuration is designed for use in a scenario where the pressure in the fluid in the drainage site 250 distal to the valve 500 (P2b) is approximately equal to or just slightly above the pressure in the reference chamber 520a (P3). For the state shown in FIG. 5, for example, the pressure P2b is relatively close to the pressure P3 inside the tube 520a, so the tube 520a tends to be in an extended or uncoiled condition, which causes the flow control membrane 540 to stretch, become more planar, and lift off the valve seat 530, thereby allowing aqueous humor to flow through the valve 500. More specifically, assuming an initial scenario of P2b significantly greater than P3, the closed end 572 of the tube 520a moves away from the center line BB as the pressure of P2b becomes less pressurized and approaches P3, thereby pulling on the membrane 540 and causing it to stretch and lift off the boss member 550, which allows fluid to flow from the fluid inlet 580 through the valve 500. Thus, the valve 500 will generally assume an open condition and permit the passage of aqueous humor into the drainage site 250 if the pressure P2b at the drainage site is not overly high in comparison to the atmospheric pressure P3.

FIG. 7 illustrates the valve 500 in a closed, flow-blocking position. The center of the flow control membrane 540 is resting on the sealing surface of the boss member 550, thereby blocking the flow of aqueous humor from the fluid inlet 580 to the fluid outlet 590 and through the drainage site 250. In the situation depicted in FIG. 7, the pressure P2b is significantly higher than the pressure P3 inside the tube 520a, so the tube 520a tends to be in a flexed or coiled condition, which causes the flow control membrane 540 to relax and the center of the membrane 540 to sag onto the boss member, thereby preventing aqueous humor from entering the valve 500 through the fluid inlet 580. More specifically, the closed end 572 of the tube 520a moves toward center line BB as the pressure of P2b rises in comparison to P3, thereby relieving strain on the membrane 540 and causing it to sag onto the boss member 550, which blocks fluid from entering the valve 500. Thus, the valve 500 will generally assume a closed condition and partially or completely block the passage of aqueous humor into the drainage site 250 if the pressure P2b at the drainage site is overly high in comparison to the atmospheric pressure P3.

Figure 8:
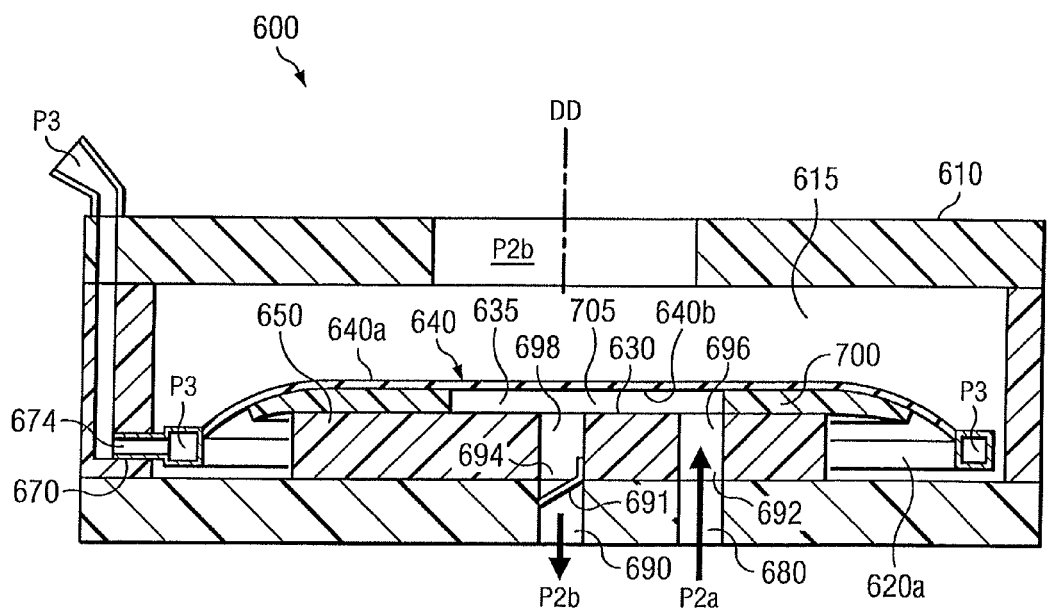
FIG. 8 is a schematic cross-sectional diagram of another exemplary pressure-driven valve in an open condition according to one embodiment of the present disclosure.

FIG. 8 illustrates a pressure-driven membrane valve 600 according to another embodiment of the present disclosure. The valve 600 does not require external power or feedback from electronic pressure sensors to operate. The valve 600 is configured to allow or block aqueous humor flowing from the anterior chamber 240 through the drainage tube 210 to any subsequent valves within the valve system 220 or to the drainage site 250. In the embodiment shown in FIG. 8, the pressure-driven membrane valve 600 includes a housing 610, reference chamber 615, a reference pressure tube 620a, a reference pressure tube 620b (not shown), a valve seat 630, a fluid flow channel 635, a flow control membrane 640, and a boss member 650. In the pictured embodiment, the components of the valve 600 are generally circular in geometry. In alternative embodiments, different geometries for the valve are contemplated, including ovoid and rectangular geometries, for example. In alternative embodiments, the valve 600 includes any number of reference pressure tubes. For example, some embodiments may include only one reference pressure tube.

The reference pressure tube 620a, the reference pressure tube 620b, and the flow control membrane 640 are interconnected in a substantially identical configuration as that shown with respect to the valve 500 illustrated in FIG. 6. The reference pressure tubes 620a, 620b are substantially similar to the reference pressure tubes 520a, 520b except for the differences noted herein. The flow control membrane 640 is shaped and configured as a substantially planar membrane having a circular shape with a diameter D1. Other shapes are also contemplated for the membrane 640, including, but not by way of limitation, rectangular or ovoid shapes. The shape of the flow control membrane 640 may be chosen depending upon spatial, pressure drop, material, and flow rate constraints. The flow control membrane 640 is securely held in place between the tubes 620a, 620b so that it will not be displaced by the force of the fluid flowing through the valve 600.

In accordance with the pictured embodiment in FIG. 6, the tubes 620a, 620b are shaped and configured as flexible, hollow tubes having a C-shaped portion 660 and a linear tail portion 670. The C-shaped portion 660 terminates in a closed end 672, and the linear tail portion terminates in an open end 674. Other shapes are also contemplated for the tubes 620a, 620b, including, but not by way of limitation, rectangular or ovoid shapes. The shape of the tubes 620a, 620b may be chosen to echo the outer shape of the flow control membrane 640. The tubes 620a, 620b may attach to the periphery of the flow control membrane 640 to form a circular configuration having an inner diameter D2. The diameter D1 of the flow control membrane 640 may be larger than the diameter D2 of the circular configuration of the tubes 620a, 620b such that the flow control membrane 640 assumes a curved, concave shape over the boss member 650.

The flow control membrane 640 is circumferentially attached at its periphery to the tubes 620a, 620b such that deformation of either of the tubes 620a, 620b, whether pressure-induced or otherwise, causes simultaneous deformation of the flow control membrane 640. The flow control membrane 640 may be attached to the tubes 620a, 620b by any of a variety of known methods, including, but not by way of limitation, welding, adhesive, and mechanical fasteners. In the pictured embodiment, only two small portions 675a, 675b of the periphery of the membrane 640 are not attached to either of the tubes 620a, 620b. Other embodiments may lack the portions 675a, 675b, or may possess smaller or larger portions 675a, 675b. The flow control membrane 640 and the tubes 620a, 620b will be more fully described below in relation to FIG. 8. The movable membrane can be fabricated integrally with some or all of the housing features by micromachining or MEMS techniques as are well known in the art using a series of material deposition, lithographic patterning and etching steps on suitable substrates. As an example, a suitable substrate may use a Si or glass wafer as a starting point, with various spacing layers of Silicon, glass, dielectric, or spin-on materials to form parts of the housing, and a flexible membrane material such as thinned silicon, silicon nitride, compliant metal such as gold, or biocompatible organic materials such as Parylene, silicone rubber, PDMS or the like, alone or in combination, in suitable thicknesses and dimensions to yield the desired performance.

Returning to FIG. 8, depicted is a cross-sectional view of the valve 600 (as taken along lines 5-5 in FIG. 6), showing the larger environment of the flow control membrane 640 and the tube 620a. The housing 610 forms an enclosure within which various other components of the valve 600, such as the flow control membrane 640, the valve seat 630, and the boss member 650, are positioned. The housing 610 includes a reference chamber 615, a fluid inlet 680, a fluid outlet 690, and the valve seat 630. The valve seat 630 is positioned between the fluid inlet 680 and the fluid outlet 690 such that fluid flows from the fluid inlet 680, through the fluid flow channel 635, and to the fluid outlet 690. In alternative embodiments, the housing 610 may be formed of separate sections that cooperate to anchor the flow control membrane 640 and the tubes 620a, 620b within the housing 610 and to form the fluid inlet 680 and the fluid outlet 690. A movable or deformable flap-valve or cantilever 691 may be present within or adjacent to the fluid outlet 690 to prevent backflow into the valve 600. The housing 610 may be constructed of any suitable biocompatible material, provided the material is able to maintain structural integrity at high internal pressures and withstand pressure changes.

The reference chamber 615 is defined by at least the housing 610, the flow control membrane 640, and the tubes 620a, 620b. The reference chamber 615 is in communication with pressure area P2b, which reflects the fluid pressure of the drainage site 250 distal the valve 600 or the pressure of the drainage site 250. In some embodiments, the reference chamber 615 is in communication with the drainage site 250 directly.

In some embodiments, the valve seat 630 may be a floor surface of the housing 610 surrounding the fluid inlet 680 and fluid outlet 690. In the pictured embodiment, the boss member 650 is positioned on the valve seat 630 such that the boss member overlies the fluid inlet 680 and the fluid outlet 690. It should be noted that some contemplated embodiments do not include the boss member 650. In a valve without a boss member, an aperture 692 of the valve seat 630 serves as the entrance to the fluid flow channel 635 and an aperture 694 of the valve seat 650 serves as the exit to the fluid flow channel 635. In a valve without a boss member, the valve seat is shaped and configured such that when the flow control membrane 640 relaxes and covers the aperture 692, the valve 600 is in a closed condition.

In the pictured embodiment in FIG. 8, the valve 600 includes a boss member 650 shaped and configured as a generally cylindrical component including an aperture 696 aligned with the fluid inlet 680 and an aperture 698 aligned with the fluid outlet 690. The boss member 650 is positioned over the valve seat 630 such that the apertures 696, 698 of the boss member 650 and the apertures 692, 694 of the valve seat 630, respectively, are co-aligned. The boss member 650 is positioned on the valve seat 630 such that the boss member 650 effectively functions as the valve seat, albeit at a raised position within the housing 610. Thus, in the embodiment pictured in FIG. 8, the aperture 696 serves as the entrance to the fluid flow channel 635 and the exit of the fluid inlet 680, and the aperture 698 serves as the exit to the fluid flow channel 635 and the entrance to the fluid outlet 690. The boss member 650 is shaped and configured such that when the flow control membrane 640 rests on the boss member 650 to cover the aperture 696, the valve 600 is in a closed condition. The boss member 650 permits increased design flexibility and flow control for the valve 600. Varying the height and other dimensions of the boss member 650 affects the amount and rate of fluid flow through the valve 600. In various embodiments, the boss member 650 may be configured as an integral extension of the valve seat 630, or may be a separate component. In some examples, the boss member 650 is an integral portion of the valve seat 630 and may be molded or machined at the same time as the valve seat 630. For some instances, the boss member may be fabricated by micromachining or MEMS techniques at the same time, or in processing steps before or after the fabrication of the valve seat feature, depending on the exact nature of the fabrication process used (such as whether the process steps used for these features are primarily additive or subtractive in nature). Other shapes are contemplated for the boss member, including, but not be way of limitation, polygonal, hemispherical, cubic, and ovoid.

Figure 9:
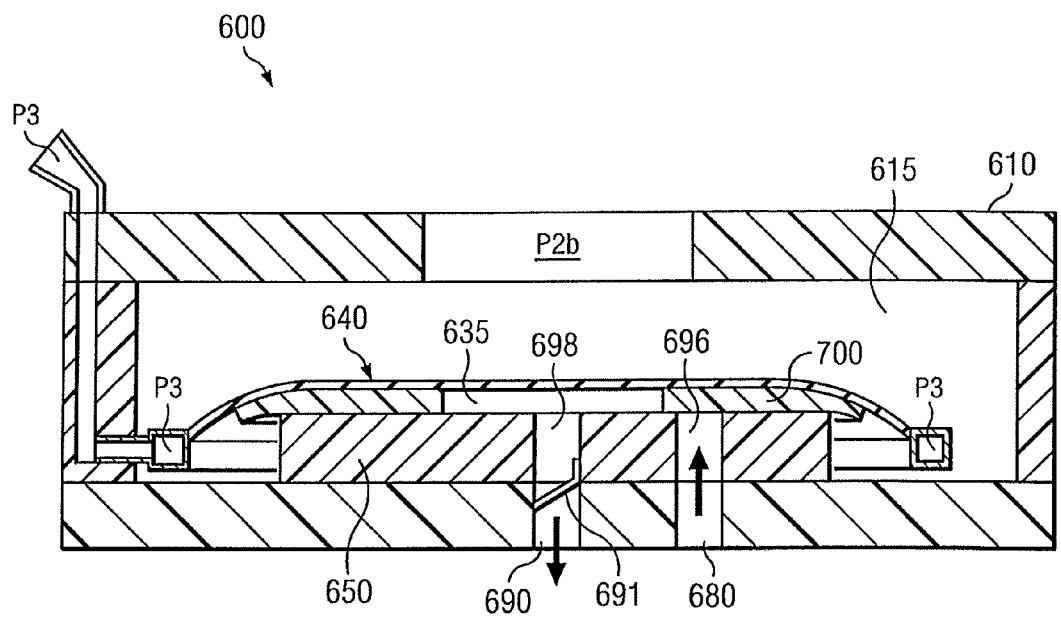
FIG. 9 is a schematic cross-sectional diagram of the exemplary pressure-driven valve shown in FIG. 8 in a closed condition according to one embodiment of the present disclosure.

The fluid flow channel 635 comprises the gap that arises between the boss member 650 (or, in embodiments without a boss member, valve seat 630) and the flow control membrane 640 when the flow control membrane 640 shifts off the aperture 696 of the boss member 650. The fluid flow channel 635 is a potential space or gap when the flow control membrane 640 covers the aperture 696 and the valve 600 is in a closed condition, as shown in FIG. 9. As shown in FIG. 8, however, the fluid flow channel 635 enlarges when the flow control membrane 640 shifts off the aperture 696 and the valve 600 is in an open condition. When the valve 600 is in an open condition, the fluid flow channel 635 is generally a constant height above the surface of the boss member 650 (i.e., the gap between the boss member 650 and the membrane 640 is generally uniform) at any given time.

The flow control membrane 640 comprises a flexible, deformable, fluid-tight membrane or diaphragm that provides valve functionality by stretching in response to the pressure-induced flexion and extension of the tubes 620a, 620b. In the pictured embodiment of FIG. 8, the membrane 640 is shown stretched over the boss member 650 such that the membrane is slightly domed or bowed over the boss member 650 at rest. The flow control membrane 640 includes two parallel sides, a side 640a and an opposite side 640b. The side 640a faces the reference chamber 615, and consequently conveys the pressure of pressure area P2b. The side 640b faces the drainage tube 210 proximal to the valve 600, and in particular the fluid inlet 680, and consequently conveys the pressure of pressure area P2a.

The side 640b of the membrane 640 includes a generally annular, washer-shaped stiffening element 700 that is fixedly attached to a peripheral zone of the side 640b. The stiffening element may be made of substantially the same material as the membrane 640, or may be made of any of a variety of other flexible or semi-flexible materials. In some embodiments, the stiffening element 700 is less flexible than the membrane 640. In some embodiments, the stiffening element is an integral portion of the membrane 640 and may be molded or machined at the same time as the membrane 640. In some embodiments, the stiffening element may be fabricated by micromachining or MEMS techniques at the same time, or in processing steps before or after the fabrication of the membrane feature, depending on the exact nature of the fabrication process used (such as whether the process steps used for these features are primarily additive or subtractive in nature).

In other embodiments, the stiffening element is a separate component that is attached to the membrane 640 by any of a variety of known methods, including welding, soldering, adhesive, and mechanical fasteners, by way of non-limiting example. Regardless of how the stiffening element 700 is attached to the membrane 640, the stiffening element 700 is configured to move laterally in unison with lateral deformation (stretching and relaxing) of the membrane 640. For example, when the membrane 640 is stretched laterally, the stiffening element 700 will shift laterally outwards (i.e., away from the center of the membrane 640) in unison with the stretching of the membrane 640 because the stiffening element is disposed on a peripheral area of the side 640b. Conversely, when the membrane 640 relaxes and/or contracts, the stiffening element 700 will shift laterally inwards (i.e., towards the center of the membrane 640) in unison with the relaxation of the membrane 640.

The stiffening element 700 creates a disc-like gap 705 between the membrane 640 and the boss member 650 that maintains the aperture 698 in an open condition. If the aperture 696 is also in an open condition, aqueous humor can flow through the valve 600. The stiffening element 700 is configured to selectively seal against the aperture 696 of the boss member 650 and thereby close or partially close the valve 600. As will be explained in further detail below, the flow control membrane 640 deforms in response to the flexion and extension of the tubes 620a, 620b to at least partially open and close the valve 600 by stretching to change the position of the stiffening element 700 relative to the aperture 696 and thereby changing the dimensions of the fluid flow channel 635. The stiffening element 700 permits increased design flexibility and flow control for the valve 600. Varying the height and other dimensions of the stiffening element 700 affects the amount and rate of fluid flow through the valve 600.

For purposes of practicality, the flow control membrane 640, including the stiffening element 700, should be thick enough to be durable and resistant to corrosion and leakage. However, the membrane 640 should also be thin enough to provide the necessary flexibility and deflection capabilities which are required in a substantially planar membrane designed for use in a pressure-responsive IOP control system 200. A preferred thickness of the flow control membrane 640 will depend on the deflection response desired for a given pressure and the material chosen. As an example, it may be fabricated out of Parylene and may have a thickness ranging from 0.5 µm to 30 µm. In other embodiments, the membrane 640 may be made of Silicon and have a thickness ranging from 0.3 µm to 10 µm. The stiffening element 700 may be thicker than the membrane 640. For example, the stiffening element 700 may have a thickness ranging from 1 µm to 200 µm. As an example, if the membrane is fabricated out of Parylene having a thickness of 3 µm, the stiffening element 700 may be made of Parylene having a thickness of 10 µm, or the stiffening element could be made of Silicon and have a thickness ranging from 3 µm to 10 µm. In some embodiments, the membrane includes annular corrugations. Membrane thickness, material, and diameter, in combination with the number, placement, and thickness of stiffening elements, and the number, placement, and depth of corrugations, all affect the cracking pressure of the valve 600.

The reference pressure tubes 620a, 620b are configured as Bourdon-style tubes, which have been long known in the prior art for the monitoring of fluid pressures, as described above in relation to the valve 500. As mentioned above, in the present disclosure, each tube 620a, 620b is substantially identical to the tubes 520a, 520b, respectively, except for the differences described herein. For simplicity of description, only one of the tubes (620a) will be described in detail and it should be understood that the tubes 620a and 620b act identically and in unison.

The reference pressure tubes 620a, 620b are anchored to the housing 610 such that the flow control membrane 640, which is attached to and suspended between the tubes 620a, 620b, may stretch and relax within the housing 610. The tubes 620a, 620b may be anchored within the housing 610 in any of a variety of known methods, provided the anchoring method does not interfere with the pressure-induced flexion or extension of the C-shaped portion 660. Similar to the tube 520a described above with reference to FIG. 6, the tube 620a comprises a hollow, flexible, curvilinear tube that is shaped and configured to include the curved, C-shaped portion 660 and the linear tail portion 670. The C-shaped portion 660 is fixedly attached to the periphery of the flow control membrane 640 such that pressure-induced deformation of the tube 620a causes simultaneous deformation of the flow control membrane 640. The linear tail portion 670 of tube 620a extends through the housing 610 such that the open end 674 is in communication with pressure area P3, which is expected to reflect atmospheric pressure. Thus, the fluid within the tube 620a conveys the pressure of pressure area P3 along the length of the tube 620a. In some embodiments, the tube 620a is in communication with the dry subconjunctiva. In alternative embodiments, the tube 620a interfaces with another portion of the eye or to atmospheric pressure directly.

The valve 600 is configured as a flow control valve that can completely or partially block the flow of aqueous humor by shifting the stiffening element 700 of the flow control membrane 640 completely or partially across the aperture 696 to block the fluid inlet 680. The housing 610 is configured to connect with drainage tube 210 such that movement the flow control membrane 640 at least partially opens and closes the lumen 215 to the outflow of aqueous humor. As described above, the position of the flow control membrane 640, and in particular the position of the stiffening element 700, determines whether the valve 600 is in an open or closed condition. When the membrane 640 relaxes and the stiffening element 700 seals against the aperture 696, the valve 600 is in a closed condition. When the membrane 640 stretches and the stiffening element 700 shifts away from the aperture 696, the valve 600 is in an open condition. The flow control membrane 640 controls the passage of aqueous humor through the valve 600 by (1) deflecting in response to pressure differences between pressure areas P2a and P2b, and (2) stretching and relaxing in response to the extension and flexion of the tubes 620a, 620b, changing the position of the stiffening element 700 relative to the aperture 696, and thereby changing the dimensions of the fluid flow channel 635 to at least partially open and close the valve 600. In some cases this latter effect should dominate the response of the valve to pressure differentials.

The flow control membrane 640 controls the passage of aqueous humor through the valve 600 in part by stretching and relaxing in response to the extension and flexion of the tubes 620a, 620b, changing the position of the stiffening element 700 relative to the aperture 696, and thereby changing the dimensions of the fluid flow channel 635 to at least partially open and close the valve 600. In particular, the C-shaped portion 660 of the tube 620a flexes and extends in response to changing pressure differentials between the fluid pressure within the tube 620a (P3) and the pressure outside the tube 620a (P2b). When the pressure outside the tube (P2b) is approximately equal to or only slightly above the pressure within the tube 620a (P3), the closed end 674 of the tube 620a extends or attempts to uncoil, thereby pulling on the membrane 640 and causing it to stretch and shift the stiffening element 700 off the aperture 696, which allows fluid to flow from the fluid inlet 680 through the fluid flow channel 635. Conversely, when the pressure outside the tube 620a (P2b) is relatively high in comparison to the pressure within the tube 620a (P3), the closed end of the tube 620a flexes or attempts to coil up, thereby relieving the strain on the membrane 640 and allowing the stiffening element 700 to cover or partially cover the aperture 696, which blocks or lowers the rate of flow through the valve 600.

In the situation depicted in FIG. 8, the valve 600 is shown in an open, flow-permitting condition. In the pictured embodiment, the components of the valve 600 are generally circular in geometry and are generally symmetric about the center line DD. In alternative embodiments, different geometries for the valve are contemplated, including ovoid and rectangular geometries, for example. In alternative embodiments, the valve 600 includes any number of reference pressure tubes. For example, in some embodiments, the valve 600 includes only one reference pressure tube.

In FIG. 8, the stiffening element 700 of the flow control membrane 640 is shifted off the aperture 696 of the boss member 650, thereby allowing the flow of aqueous humor from the fluid inlet 680, through the fluid flow channel, to the fluid outlet 690. A valve 600 having this configuration is designed for use in a scenario where the pressure in the fluid in the drainage site 250 or the drainage tube 210 distal to the valve 600 (P2b) is approximately equal to or only slightly above the pressure in the reference chamber 620a (P3). In FIG. 8, for example, the pressure P2b is approximately the pressure P3 inside the tube 620a, so the tube 620a tends to be in an extended or uncoiled condition, which causes the flow control membrane 640 to stretch laterally, and shift the stiffening element laterally off the aperture 696, thereby allowing aqueous humor to flow through the valve 600. More specifically, assuming an initial scenario of a P2b significantly above P3, the closed end 672 of the tube 620a moves away from the centerline DD as the pressure P2b decreases and becomes approximately equal to P3, thereby pulling on the membrane 640 and causing it to stretch and shift the stiffening element 700 off the aperture 696, which allows fluid to flow from the fluid inlet 680 through the valve 600. Thus, the valve 600 will generally assume an open condition and permit the passage of aqueous humor into the drainage site 250 if the pressure P2b at the drainage site is not overly high in comparison to the atmospheric pressure P3.

FIG. 9 illustrates the valve 600 in a closed, flow-blocking position. The stiffening element 700 of the flow control membrane 640 is shifted onto the aperture 696 of the boss member 650, thereby blocking the flow of aqueous humor from the fluid inlet 680 into the fluid flow channel 635. In the situation depicted in FIG. 9, the pressure P3 inside the tube 620a is relatively low compared to the pressure P2b, so the tube 620a tends to be in an flexed or coiled condition, which causes the flow control membrane 640 to relax, and shift the stiffening element laterally onto the aperture 696, thereby blocking the flow of aqueous humor from entering the valve 600 through the fluid inlet 680. More specifically, the closed end 672 of the tube 620a moves away from the centerline DD as the pressure of P2b rises in comparison to P3, thereby relieving strain on the membrane 640 and causing the stiffening element 700 to shift toward the center of the membrane 340 and cover the aperture 696, which blocks aqueous humor from entering the valve 600. Thus, the valve 600 will generally assume a closed condition and block the passage of aqueous humor into the drainage site 250 if the pressure P2b at the drainage site is overly high in comparison to the atmospheric pressure P3.

Figure 10:
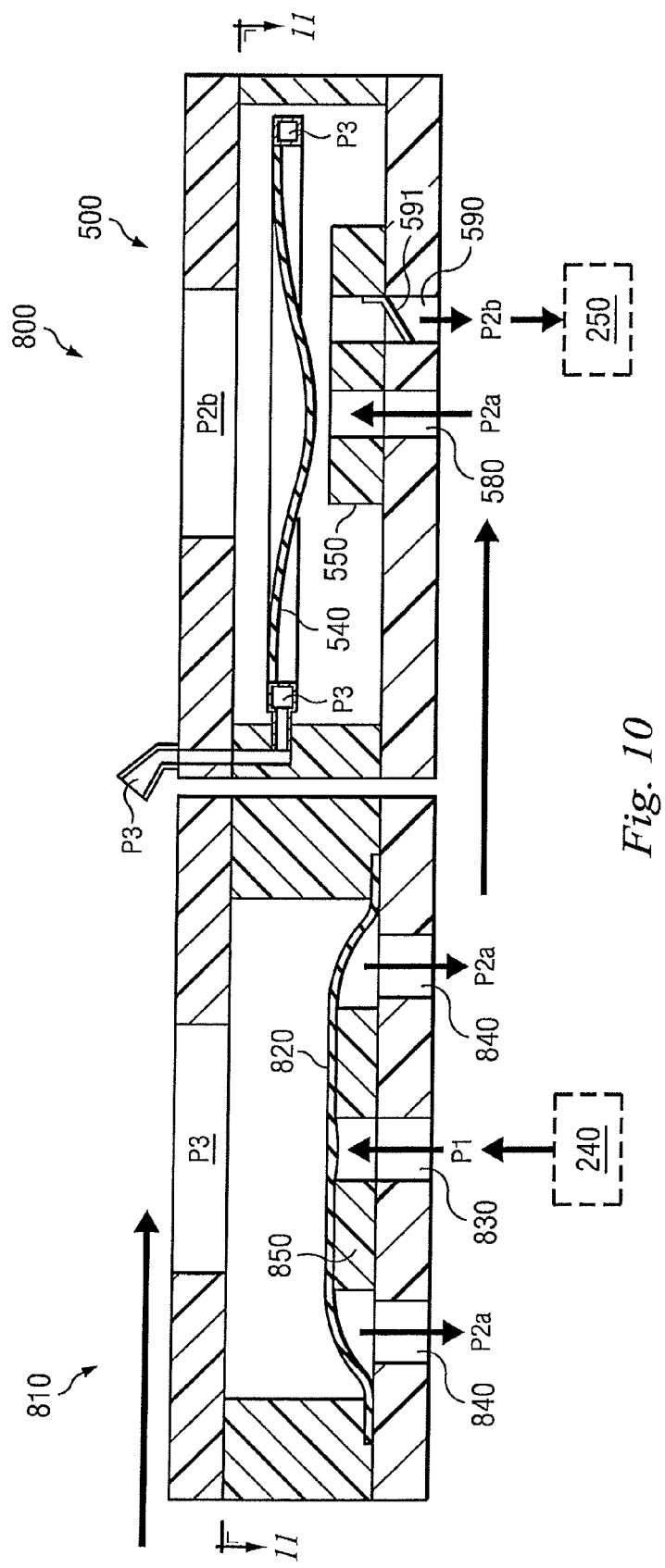
FIG. 10 is a schematic cross-sectional diagram of an exemplary valve system including the exemplary pressure-driven valve shown in FIGS. 6 and 7 for use in an exemplary IOP control system according to one embodiment of the present disclosure.

FIG. 10 is a schematic cross-sectional diagram of an exemplary valve system 800 including the exemplary pressure-driven valve 500 shown in FIGS. 6 and 7 for use in an exemplary IOP control system according to one embodiment of the present disclosure. The valve system 800 includes two pressure-driven membrane valves, a valve 810 and a valve 500, configured to operate in series. The valve 810 controls the entry of fluid from the fluid inlet 830 through the valve 810 in response to the pressure differential between the fluid anterior to the valve 810, reflected by P1, and atmospheric pressure, reflected by P3. The valve 810 includes a membrane 820 that deflects in response to the pressure differential between pressure areas P1 and P3 to allow or block aqueous humor from flowing from the anterior chamber 240 through the valve 810 towards the valve 500. The valve 810 further includes a fluid inlet 830, a fluid outlet 840, and a boss member 850.

The valve 810 may include a secondary path to an override pressure relief valve (not shown), which may be a membrane valve configured to allow flow at a higher pressure differential than the valve 810. This secondary pressure relief valve may be two-staged to guard against catastrophic eye depressurization if one stage fails. The pressure area P2a reflects the pressure of the fluid flowing from the valve 810 towards the valve 500. The pressure area P2b reflects the pressure of the fluid distal the valve 500 or at the drainage site 250. The valve 500 may control the entry of fluid from the fluid inlet 580 through the valve 500 in response to the pressure differential between pressure areas P2a and P2b, as well as to the pressure differential between pressure areas P2b and P3. The valve 500 includes the flow control membrane 540, the boss member 550, the fluid inlet 580, the fluid outlet 590, and the cantilever 591. The cantilever 591 within the fluid outlet 590 may function as a check valve to prevent backflow of fluid into the valve 500. Other embodiments of a valve system according to the present disclosure may include the valve 300, the valve 600, or any of a variety of other dual-input membrane valves instead of or in addition to valve 500. The valve system also may include single-membrane valves, electrically controlled valves, or other flow controlling devices including, by way of non-limiting example, valves or pumps.

Figure 11:
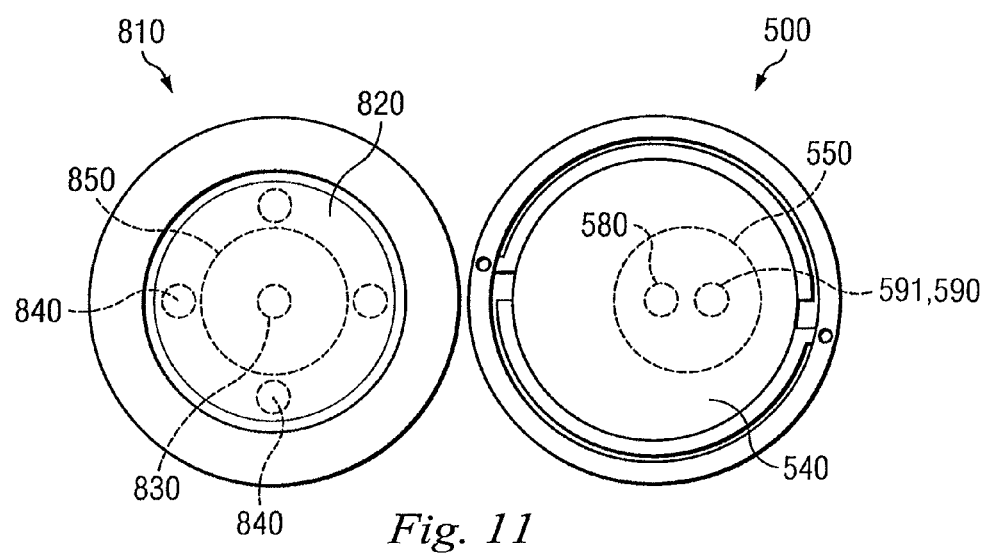
FIG. 11 is a schematic showing a top plan view of the exemplary valve system shown in FIG. 10 for use in an exemplary IOP control system according to one embodiment of the present disclosure.

FIG. 11 is a diagrammatic cross-sectional view of an embodiment of the exemplary valve system 800 shown in FIG. 10 according to the present disclosure. FIG. 11 depicts a cross-section through lines 11-11 in FIG. 10 showing the valve system 800 including a P1:P3 valve 810 and a P2:P3 valve 500. The valve 810 includes the circular flow control membrane 820, the fluid inlet 830, four fluid outlets 840, and the boss member 850. The fluid inlet 830 is positioned centrally aligned with and under the membrane 820. The fluid outlets 840 are also positioned under the membrane 820. The valve 500 includes the circular flow control membrane 540, the fluid inlet 580, the fluid outlet 590, the cantilever 591, and the boss member 550. The fluid inlet 580 and the fluid outlet 590 are positioned under a peripheral portion of the membrane 540. Aqueous humor may flow into the valve 810 through the fluid inlet 830, exit through the fluid outlets 840, enter the valve 500 through the fluid inlet 580, and exit through the fluid outlet 590. The cantilever 591 may prevent backflow of aqueous humor into the valve system 800.

Though the pressure-driven valves described in the present disclosure are depicted as comprising disk-like flow control membranes and boss members, the valves may be comprised of any of a number of different flow control elements that meter, restrict, or permit the flow of aqueous humor from the anterior chamber 240 to the drainage site 250. In some embodiments, the flow control membranes of the valves described in the present disclosure may be in contact with a biocompatible gel to transmit pressure from the aqueous humor at a region of interest. The biocompatible gel may be one of a variety of biocompatible gels, including silicone dielectric gels used with medical grade piezoresistive pressure sensors. These modifications prevent the formation of solid fibers as a result of the proteinaceous content of the aqueous humor, which could mechanically disrupt valve operation. In addition, the pressure-driven valves described herein may be positioned anywhere in fluid communication with the drainage tube 210, whether within or along the drainage tube 210. Moreover, to ensure biocompatibility, the pressure-driven valves described herein can be coated or encapsulated in a biocompatible material including, but not by way of limitation, polypropylene, silicone, parylene, or other known biocompatible materials.

Conventional passive check valves in drainage device implants (e.g., the Ahmed Valve) provide a reduced risk of hypotony in the weeks immediately following surgery. But these conventional valves have no mechanism for accounting for drainage site or bleb pressure. The systems disclosed herein may adjust to control flow to the bleb. Accordingly, the systems and methods disclosed herein provide a device that a) requires zero to minimal power (internal or external), and b) presents a mechanism of minimizing bleb height (reducing or eliminating bleb) by controlling the flow through the IOP control system 200 based on pressure differentials, which could significantly reduce the effect of fibrosis and also reduce or eliminate other issues related to bleb management.

The systems and methods described herein achieve IOP control with a very small device that utilizes zero to very low power. The system takes into account bleb pressure in regulating drainage flow. Accordingly, based on pressure-driven valves and an optional electronic pump to control the flow rate of aqueous humor, the system provides suitable care for a patient suffering from irregular intraocular pressure.

Embodiments in accordance with the present disclosure may be used in a variety of applications to regulate flow and/or pressure. For example, but not by way of limitation, embodiments of the present disclosure may be utilized to regulate flow and/or pressure as part of a microanalytical system, a dialysis system, a process control system, a drug delivery system, a solar thermal system, a cooling system, and/or a heating system. In addition, embodiments of the present disclosure may be utilized to regulate pressure and/or flow in a variety of fluidic systems such as, but not by way of limitation, the urinary tract, the brain (e.g., to regulate intracranial pressure), and the circulatory/renal system (e.g., as part of a dialysis system). Moreover, some embodiments are shaped and configured for implantation in a patient, while others are not.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A pressure-driven valve, comprising:
   a housing comprising a fluid inlet and a fluid outlet; and
   a flow control portion disposed within the housing, the flow control portion having a first side subject to fluid flow pressure in a fluid flow channel, and having a second side subject to an outlet pressure representative of pressure at the fluid outlet, the flow control portion being deformable to increase and decrease flow through the fluid flow channel based on pressure differentials between the fluid flow pressure, a tube pressure, and the outlet pressure, and wherein the flow control portion has a flow control membrane and a radially-fluctuating pressure tube attached to the periphery of the flow control membrane, wherein the pressure tube comprises a hollow, flexible, curved deformable tube including a closed end and an open end, the pressure tube being filled with fluid conveying the tube pressure, the pressure tube being curved to define a circular space having a first diameter, and wherein the pressure tube is deformable in response to pressure differentials between the outlet pressure and the tube pressure, thereby deforming the flow control membrane to increase and decrease flow through the fluid flow channel.

2. The valve of claim 1, wherein the pressure tube is filled with fluid conveying an atmospheric pressure.

3. The valve of claim 2, wherein the flow control portion and the housing are configured to restrict flow when the outlet pressure is substantially higher than the atmospheric pressure.

4. The valve of claim 1, wherein the flow control portion further includes a stiffening element, the stiffening element attached to the flow control membrane on the first side of the flow control portion and configured to shift in response to the deformation of the flow control portion to selectively open and close the valve.

5. The valve of claim 1, wherein the pressure tube is configured to deform in response to the pressure differential between the tube pressure and the outlet pressure, thereby deforming the flow control membrane from a first diameter to a second diameter to affect the size of the fluid flow channel.

6. A pressure-driven valve for implantation in a patient, comprising:
   a housing comprising a fluid inlet and a fluid outlet;
   a fluid flow channel extending between the fluid inlet and the fluid outlet;
   a pressure tube disposed within the housing, the pressure tube comprising a hollow, flexible, curved tube including a closed end and an open end, the pressure tube being filled with fluid conveying a tube pressure, the pressure tube being curved to define a circular space having a first diameter; and
   a deformable portion attached to the pressure tube, the deformable portion defining a portion of the fluid flow channel and being configured to deform to increase and decrease a size of the fluid flow channel to regulate fluid flow from the fluid inlet to the fluid outlet, the deformable portion being disposed and arranged to deform as a result of pressure differentials between the tube pressure, a fluid flow channel pressure, and an outlet pressure representative of fluid pressure at the fluid outlet.

7. The valve of claim 6, wherein the deformable portion comprises a flow control membrane attached at its periphery to the pressure tube and disposed within the space, the flow control membrane forming a reference chamber on a first side of the flow control membrane and the fluid flow channel on a second opposing side of the membrane, the reference chamber having the outlet pressure, and wherein deformation of the flow control membrane increases and decreases the size of the fluid flow channel.

8. The valve of claim 7, wherein the flow control membrane is circumferentially attached to the pressure tube.

9. The valve of claim 7, wherein the flow control membrane includes corrugations.

10. The valve of claim 7, further including a valve seat positioned within the housing between the fluid inlet and the fluid outlet, the deformable portion selectively engaging the valve seat to affect flow in the fluid flow channel.

11. The valve of claim 10, wherein the valve seat is a boss.

12. The valve of claim 7, wherein the pressure tube is configured to control flow though the fluid flow channel by deforming in response to the pressure differential between the tube pressure and the outlet pressure, thereby deforming the flow control membrane to selectively open and close the fluid flow channel.

13. The valve of claim 7, wherein the flow control membrane is configured to control the fluid flow channel by deforming in response to the pressure differential between the outlet pressure and the fluid flow channel pressure.

14. The valve of claim 7, wherein the flow control membrane comprises a flexible, liquid-tight membrane configured to deflect away from a higher pressure toward a lower pressure in the absence of other forces acting on the membrane.

15. The valve of claim 7, wherein the pressure tube is configured to control flow though the fluid flow channel by deforming in response to the pressure differential between the tube pressure and the outlet pressure, thereby deforming the flow control membrane from a first diameter to a second diameter to affect the size of the fluid flow channel.

16. The valve of claim 7, wherein the flow control membrane includes a stiffening element disposed on the second opposing side of the flow control membrane.

17. The valve of claim 16, wherein the stiffening element comprises an annular shape.

18. The valve of claim 16, wherein the pressure tube is configured to control flow though the fluid flow channel by deforming in response to the pressure differential between the tube pressure and the outlet pressure, thereby deforming the flow control membrane to shift the position of the stiffening element relative to the fluid inlet to selectively open and close the fluid flow channel.

* * * * *